(12) United States Patent
Cohen

(10) Patent No.: US 8,197,868 B2
(45) Date of Patent: *Jun. 12, 2012

(54) **PROCESS OF MAKING PURIFIED EXTRACT OF *SCUTELLARIA BARBATA* D. DON**

(75) Inventor: Isaac Cohen, Piedmont, CA (US)

(73) Assignee: BioNovo, Inc., Emeryville, CA (US)

( * ) Notice: Subject to any disclaimer, the term of this patent is extended or adjusted under 35 U.S.C. 154(b) by 588 days.

This patent is subject to a terminal disclaimer.

(21) Appl. No.: 12/274,236

(22) Filed: Nov. 19, 2008

(65) Prior Publication Data

US 2009/0130237 A1 May 21, 2009

Related U.S. Application Data

(60) Provisional application No. 60/989,059, filed on Nov. 19, 2007.

(51) Int. Cl.
*A61K 36/53* (2006.01)

(52) U.S. Cl. .................................... 424/741

(58) Field of Classification Search .................. None
See application file for complete search history.

(56) References Cited

U.S. PATENT DOCUMENTS

| | | | |
|---|---|---|---|
| 5,032,580 A | 7/1991 | Watanabe et al. | |
| 5,164,182 A | 11/1992 | Meybeck et al. | |
| 5,650,433 A | 7/1997 | Watanabe et al. | |
| 5,874,084 A | 2/1999 | Yng-Wong | |
| 6,238,707 B1 | 5/2001 | Chun | |
| 6,280,715 B1 | 8/2001 | Seguin et al. | |
| 6,309,825 B1 | 10/2001 | Thomas | |
| 6,348,204 B1 | 2/2002 | Touzan | |
| 6,551,627 B1 | 4/2003 | Yoon et al. | |
| 6,599,540 B1 | 7/2003 | Fabre et al. | |
| 7,700,136 B2 | 4/2010 | Cohen | |
| 2002/0094350 A1 | 7/2002 | Wong | |
| 2003/0170292 A1 | 9/2003 | Yong et al. | |
| 2003/0190375 A1 | 10/2003 | Erdelmeier et al. | |
| 2004/0101576 A1 | 5/2004 | Yagi et al. | |
| 2005/0032882 A1 | 2/2005 | Chen | |
| 2005/0118290 A1 | 6/2005 | Yong et al. | |
| 2005/0196409 A1 | 9/2005 | Dao et al. | |
| 2005/0208070 A1 | 9/2005 | Dao et al. | |
| 2005/0208159 A1 | 9/2005 | Kang et al. | |
| 2005/0260285 A1 | 11/2005 | DiMateeo-Leggio | |
| 2005/0267193 A1 | 12/2005 | Zelig | |
| 2006/0100238 A1 | 5/2006 | Kelly et al. | |
| 2006/0134243 A1 | 6/2006 | Cohen | |
| 2006/0134245 A1 | 6/2006 | Cohen | |
| 2006/0165821 A1* | 7/2006 | Zhang et al. .................. 424/741 |
| 2006/0166231 A1 | 7/2006 | Baker et al. | |
| 2006/0210657 A1 | 9/2006 | Chou | |
| 2006/0222721 A1 | 10/2006 | Cohen | |
| 2007/0050865 A1 | 3/2007 | Ayabe | |
| 2007/0105133 A1 | 5/2007 | Clarke et al. | |
| 2007/0110832 A1 | 5/2007 | Cohen | |
| 2007/0122492 A1 | 5/2007 | Behr et al. | |
| 2007/0122501 A1 | 5/2007 | Harley et al. | |
| 2007/0203136 A1 | 8/2007 | Lu et al. | |
| 2007/0265318 A1 | 11/2007 | Greenlee et al. | |
| 2008/0069909 A1 | 3/2008 | Olalde | |
| 2008/0319051 A1 | 12/2008 | Cohen | |
| 2009/0041867 A1 | 2/2009 | Cohen | |
| 2009/0042818 A1 | 2/2009 | Cohen | |
| 2009/0068293 A1 | 3/2009 | Cohen | |
| 2009/0068298 A1 | 3/2009 | Cohen | |
| 2009/0068299 A1 | 3/2009 | Cohen | |
| 2009/0258942 A1 | 10/2009 | Cohen | |
| 2009/0304825 A1 | 12/2009 | Cohen | |
| 2009/0311349 A1 | 12/2009 | Cohen | |
| 2009/0312274 A1 | 12/2009 | Cohen | |
| 2009/0312437 A1 | 12/2009 | Cohen | |

FOREIGN PATENT DOCUMENTS

| | | |
|---|---|---|
| CN | 1183297 A | 6/1998 |
| CN | 1294009 A | 5/2001 |
| CN | 101073600 A | 11/2007 |
| EP | 0499467 A2 | 9/1992 |
| JP | 2001-122871 | 5/2001 |
| JP | 2002-029980 | 1/2002 |
| JP | 2002284696 A | 10/2002 |
| JP | 2004-155779 | 6/2004 |
| KR | 10-0221762 B1 | 9/1999 |
| KR | 10-2003-0006736 | 1/2003 |
| KR | 10-2003-0027208 | 4/2003 |
| KR | 10-2006-0057291 | 5/2006 |

(Continued)

OTHER PUBLICATIONS

Wong et al. "Oldenlandia diffusa and *Scutellaria barbata* Augment Macrophage Oxidative Burst and Inhibit Tumor Growth", Cancer Biotherapy and Radiopharmaceuticals, vol. 11, No. 1, 1996, pp. 51-56.*

Sheng-Jun Dai et al. "Neo-Clerodane diterpenoids from *Scutellaria barbata* with cytotoxic activities", Phytochemistry, vol. 67, (2006), pp. 1326-1330.*

Chrzan et al., "Phytoestrogens activate estrogen receptor β1 and estrogenic responses in human breast and bone cancer cell lines," Mol. Nutr. Food Res. 51:171-177 (2007).

Guo et al., "Anticancer effect of aloe-emodin on cervical cancer cells involves G2/M arrest and inductions of differentiation," Acta Pharmacol. Sin. 28(12):1991-1995 (2007).

(Continued)

*Primary Examiner* — Christopher R. Tate
*Assistant Examiner* — Deborah A. Davis
(74) *Attorney, Agent, or Firm* — Wilson, Sonsini, Goodrich & Rosati

(57) ABSTRACT

An extract of *Scutellaria barbata* D. Don is effective in the arrest of cancer cell growth in the G1 phase, the induction of apoptosis in cancer cells and the shrinking of solid cancers. The extract may be prepared as a pharmaceutical composition for administration to mammals for the treatment of solid cancers, such as epithelial cancers. Such epithelial cancers include breast cancer and ovarian cancers. The extract is obtained from *Scutellaria barbata* D. Don by contacting aerial portions of a plant from the species *Scutellaria barbata* D. Don with an aqueous or alcoholic solvent.

16 Claims, 9 Drawing Sheets

FOREIGN PATENT DOCUMENTS

| WO | WO-03-040134 A | 5/2003 |
|---|---|---|
| WO | WO-2005-044182 A2 | 5/2005 |
| WO | WO-2006-065599 A1 | 6/2006 |
| WO | WO-2006-065608 A2 | 6/2006 |
| WO | WO-2008-011073 A2 | 1/2008 |

OTHER PUBLICATIONS

Harris et al., "Phytoestrogens Induce Differential Estrogen Receptor Alpha- or Beta-Mediated Responses in Transfected Breast Cancer Cells," Exp. Biol. Med. 230(8):558-568 (2005.

Matsuda et al., "Phytoestrogens from the roots of Polygonum cuspidatum (polygonaceae): structure-Requirement of hydroxyanthraquinones for estrogenic activity," Bioorganic and Medicinal Chemistry Letters 11(14):1839-1842 (2001).

Mueller et al., "Occurrence of Emodin, Chrysophanol and Physcion in Vegetables, Herbs and Liquors," Food and Chemical Toxicology 37(5):481-484 (1999).

Srinivas et al., "Emodin induces apoptosis of human cervical cancer cells through poly(ADP-ribose) polymerase cleavage and activation of caspase-9," Eur. J. Pharmacology 473:117-125 (2003).

PCT/US09/040557 Search Report dated Dec. 14, 2009.
PCT/US09/042915 Search Report dated Dec. 22, 2009.
PCT/US09/003427 Search Report dated Jan. 18, 2010.
PCT/US09/46496 Search Report dated Jan. 12, 2010.
EP05853254 Supplementary Search Report dated Jun. 11, 2009.
PCT/US08/84079 Search Report dated Jun. 24, 2009.
PCT/US05/44362 Search Report dated Jun. 22, 2006.

Albert, A. et al., "Efficacy and safety of phytoestrogen preparation derived from Glycine max (L.) Merr in climacteric symptomatology: a multicentric, open, prospective and non-randomized trial," Phytomedicine 9:85-92 (2002).

An, J. et al., "Estrodiol repression of tumor necrosis factor-alpha transcription requires estrogen receptor activation function-2 and is enhanced by coactivators," PNAS USA 96:15161-15166 (1999).

An, J. et al., "Estrgen receptor beta-selective transcriptional activity and recruitment of coregulators by phytoestrogens," J. Biol. Chem. 276:17808-17814 (2001).

Anderson, G.L. et al., Effects of conjugated equine estrogen in postmenopausal women with hysterectomy: the Women's Health Initiative randomized controlled trial, JAMA 291:1701-1712 (2004).

Baek, J. et al., "Effects of Methyl Chloride (MC) Fraction Isolated from Scutellaria barbata on Apoptosis of a Human Lymphoma Cell Line (U937) Cells," Blood 100(11):279B, Abstract 4650 (2002).

Barbieri, RL "The initial fertility consultation: Recommendations concerning cigarette smoking, body mass index, and alcohol and caffeine consumption" American Journal of Obstetrics and Gynecology vol. 185, No. 5 (Nov. 2001) 1168-1173.

Barkhem, T. et al., "Differential response of estrogen receptor alpha and estrogen receptor beta to partial estrogen agonists/antagonists," Mol. Pharma. 54:105-112 (1998).

Bensky, D. et al., Chinese Herbal Medicine: Formulas & Strategies (1990), Eastland Press, Inc., Seattle, Washington, pp. 117, 224, 379, 380, 383 and 384.

Bernhardt, et al., "Standardized Kinetic Microassay to Quantify Differential Chemosensitivity on the Basis of Proliferative Activity," J. Cancer Res. Clin Oncol 118:35-43 (1992).

Bjornstrom, L., "Estrogen receptor-dependent activation of AP-1 via non-genomic signalling," Nuclear Receptor 2:3 (2004).

Campbell, M.J. et al., "Antiproliferative Activity of Chinese Medicinal Herbs on Breast Cancer Cells In Vitro," Anticancer Research 22:3843-3852 (2002).

Chlebowski, R.T. et al., "Influence of estrogen plus progestin on breast cancer and mammography in healthy postmenopausal women: the Women's Healt Initiative Randomized Trial, " JAMA 289:3243-3253 (2003).

Chui, C.H. et al., "Anti-cancer potential of traditional Chinese herbal medicines and microbial fermentation products," Minerva Biotech 17:183-191 (2005).

Chui, C.H. et al., "Activities of fresh juice of Scutellaria barbata and warmed water extract of Radix Sophorae Tonkinensis on anti-proliferation and apoptosis of human cancer cell lines," Intl J Mol Med 16:337-341 (2005).

Coope J. "Hormonal and non-hormonal interventions for menopausal symptoms" Maturitas, vol. 23 No. 2 (Mar. 1996) 159-168.

Cranney, A. and Adachi, J.D., "Benefit-risk assessment of raloxifene in postmenopausal osteoporosis," Drug Saf. 28:721-730 (2005).

Cvoro, A. et al., "Selective activation of estrogen receptor-beta transcriptional pathways by an herbal extract," Endocrinology 148:538-547 (2007).

Cvoro, A. et al., "Distinct Roles of Unliganded and Liganded Estrogen Receptors in Transcriptional Repression," Mol. Cell 21:555-564 (2006).

Delmas, P. et al., "Effects of raloxifene on bone mineral density, serum cholesterol concentrations, and uterine endometrium in postmenopausal women," N. Eng. J. Med. 337:1641-1647 (1997).

Ducki, S. et al., "Isolation of E-1-(4'-Hydroxypheny1)-but-1-en-3-one from Scutellaria barbata," Planta Medica 62:185-186 (1996).

Duffy, R. et al., "Improved cognitive function in postmenopausal women after 12 weeks of consumption of a soya extract containing isoflavones," Pharacol. Biochem. Behavior 75(3):721-729 (2003).

Evans, M.L. et al., "Management of postmenopausal hot flushes with venlafaxine hydrochloride: a randomized, controlled trial," Obstet. Gynecol. 105:161-166 (2005).

Ferrier, R.J. and Blatter, R., "NMR SPectroscopy and Conformational Features, Ch. 21, Carbohydrate Chemistry-Monosaccharides, Disaccharides and Specific Oligosaccharides: A Review," pub. Royal Society of Chemistry, vol. 32:312-314 (2001).

Fingl, et al., in The Pharmacological Basis of Therapeutics (Ed. Goodman & Gilman, MacMillan, NY) Chapter 1, p. 1 (1975).

Fong et al., "Poster Presentation," Proceedings of the American Association for Cancer Research 95th Annual Meeting, 2007 AACR Annual Meeting, Apr. 14-18, 2007, Los Angeles, Abstract 4837.

Fu, B. et al., "Isolation and identification of flavonoids in licorice and a study of their inhibitory effects on tyrosinase," J. Agric. Food Chem. 53:7408-7414 (2005).

Goh, D. et al., "Inhibitory Effects of a Chemically Standardized Extract from Scutellaria barbata in Human Colon Cancer Cell Lines, LoVo," J Agric. Food Chem. 53:8197-8204 (2005).

Haber, "Chromatin Immunoprecipitation," Jul. 18, 2005 http://www.bio.brandeis.edu/haberlab.jehsite/protocol.html.

Harris, H.A. et al., "Evaluation of an estrogen receptor-beta agonist in animal models of human disease," Endocrinology 144:4241-4249 (2003).

Hewitt, S.C. et al., "Lessons in estrogen biology from knockout and transgenic animals," Annu. Rev. Physiol. 67:285-308 (2005).

Hsu, H.Y. et al., Oriental Materia Medica: A Concise Guide (1986):Keats Publishing Inc., USA, pp. 119, 120, 144, 145, 272, 273, 524 and 525.

Jordan, V.C., "Selective estrogen receptor modulation: concept and consequences in cancer," Cancer Cell 5:207-213 (2004).

Jordan, V.C., "The ups and downs of the estrogen receptor," J. Clin, Onc. 21:3-4 (2004).

Kim, D. et al., "Regulation of IGF-1 production and proliferation of human leiomyomal smooth muscle cells by Scutellari barbata D. Don in vitro: isolation of flavonoids of apigenin and luteolon as acting compounds," Toxicology and Applied Pharmacology 205:213-224 (2005).

Klein, O.K. et al., "Estrogen bioactivity in fo-ti and other herbs used for their estrogen-like effects as determined by a recombinant cell bioassay," J. Clin. Endocrin. Metab. 88:4077-4079 (2003).

Klinge, C.M., "Estrogen receptor interaction with estrogen response elements," Nucleic Acids Res. 29(14):2905-2919 (2001).

Kuiper, G.G. et al., "Interaction of estrogenic chemicals and phyytoestrogens with estrogen receptor beta," Endocrinology 139:4252-4263 (1998).

Kummalue, T., "Molecular Mechanism of Herbs in Human Lung Cancer Cells," J. Med. Assoc.Thai. 88(11):1725-1734 (2005).

Lacroix, M. And Leclercq, G., "Relevance of breast cancer cell lines as models for breast tumors: an update," Breast Cancer Res. Treat. 83:249-289 (2004).

Laganiere, J. et al., "Locational analysis of estrogen receptor alpha target promoters reveals that FOXA1 defines a domain of the estrogen response," PNAS 102(33):11651-11656 (2005).

Lawrence, N.J. et al., "The Chemistry and Biology of Antimitotic Chalcones and Related Enone Systems," Current Pharmaceutical Design 11:1670-1693 (2005).

Lee, T.K. et al., "*Scutellaria barbata* D.Don induces c-fos gene expression in human uterine leiomyomal cells by activating β2-adrenergic receptors," Int. J. Gynecol. Cancer 14:526-531 (2004).

Lee, T.K. et al., "Inhibitory effects of *Scutellaria barbata* D. Don on human uterine leiomyomal smooth muscle cell proliferation through cell cycle analysis," Intl. Immunol. 4:447-454 (2004).

Levy, N. et al., "Multiple Transcription Factor Elements Collaborate with ER(alpha) to Activate an Inducible Estrogen Response Element in the NKG2E gene," Endocrinoloy 148(7):3449-3458 (2007).

Liu, C.W. et al., "Estrogen receptor assays of Scutellariae Barbatae Herba, Lithospermix Radix and Oldenlandiae Herba," Pharm. Res. 12(Suppl.):s126 (1995).

Loprinzi, C.L., et al., "Venlafaxine in management of hot flashes in survivors of breast cancer: a randomised controlled trial," Lancet 356:2059-2063 (2000).

Loprinzi, L. et al., "Pilot evaluation of gabapentin for treating hot flashes," Mayo Clin. Proc. 77:1159-1163 (2002).

Love, R. et al., "Effects of tamoxifen on bone mineral density in postmenopausal women with breast cancer," N. Engl. J. Med. 326:852-856 (1992).

Lu, H.C., Chinese Herbs with Common Foods:Recipes for Health and Healing (1997), Japan; Kodansha International Inc., pp. 94, 115, 119, and 120.

MacGregor, J.I. and Jordan, V.C., "Basic Guide to the Mechanisms of Antiestrogen Action," Pharmacol. Rev. 50(2):151-196 (1998).

Maggioline, M. et al., "Estrogenic and antiproliferative activities of isoliquiritigenin in MCF7 breast cancer cells," J. Steroid Biochem. Mol. Biol. 82:315-322 (2002).

Manson, J.E. et al., "Estrogen plus progestin and the risk of coronary heart disease," N. Engl. J. Med. 349:523-534 (2003).

Marsh, M.M. et al., "Protection against atherosclerosis by estrogen is independent of plasma cholesterol levels in LDL receptor-deficient mice," J. Lipid Res. 40:893-900 (1999).

McHenry, A.M. et al., "Modulation of apoptosis in LNCaPcells by the Chinese medicinal herb *Scutellaria barbata*," Aacr Meeting Abstracts Online, Abstract 721, Proc. Amer. Assoc. Cancer Res. 45 (2004) http://.www.aacrmeetingabstacts.org/cpi/content/abstract/2004/1/167.

Miller, H. et al., "Modulation of estrogen signaling by interaction of heat shock protein 27, a biomarker for atherosclerosis, and estrogen receptor beta: mechanistic insight into the vascular effects of estrogens," Atheroscler. Thromb. Vasc. Biol. 25:10-14 (2005).

Newman, et al., "Natural Products as Sources of New Drugs Over the Period 1981-2002," J. Nat. Prod 66:1022-1037 (2003).

Nilsson, S. and Gustafsson, J.A., "Estrogen receptor transcription and transactivation: basic aspects of estrogen action," Breast Cancer Res. 2:360-366 (2000).

Parmar, H. et al., "A novel method for growing human breast epithelium in vivo using mouse and human mammary fibroblasts," Endocrinology 143:4886-4896 (2002).

Paruthiyil, S. et al., "Estrogen receptor beta inhibits human breast cancer cell proliferation and tumor formation by causing a G2 cell cycle arrest," Cancer Res. 64:423-428 (2004).

Powell, C.B. et al., "Aqueous extract of herba *Scutellaria barbatae*, a chinese herb used for ovarian cancer, induces apoptosis of ovarian cancer cell lines," Gynecologic Oncology 91:332-340 (2003).

Ricke, W.A. et al., "Steroid hormones stimulate human prostate cancer progression and metastasis," Int. J. Cancer 118:2123-2131 (2006).

Rossouw, J.E. et al., "Postmenopausal hormone therapy and risk of cardiovascular disease by age and years since menopause," JAMA 297:1465-1477 (2007).

Rugo, H. et al., "Phase I trial and antitumor effects of BZL101 for patients with advanced breast," Breast Cancer Res Treat 105(1):17-28 (2007) DOI 10.1007/s10549-006-9430-6, Springer Science-Business Media B.V. 2006.

Sato, S. et al., "Total Synthesis of three naturally occuring 6,8-di-C-glycosylflavanoids: phloretin, naringenin, and apigenin bis-C-b-D-glucosides," Carbohydrate Res. 341:964-970 (2006).

Semmar, N. et al., "New flavonol tetraglycosides from Astragalus caprinus," Chem. Pharm, Bull. 50(7):981-984 (2002).

Shoemaker, M. et al., "In Vitro Anticancer Activity of Twelve Chinese Medicinal Herbs," Phytotherapy Research 19:649-651 (2005).

Shumaker, S.A. et al., Conjugated equine estrogens and incidence of probable dementia and mild cognitive impairment in postmenopausal women: Women's Health Initiative Memory Study,: JAMA 291:2947-2958 (2004).

Shumaker, S.A. et al., "Estrogen plus progestin and the incidence of dementia and mild cognitive impairment in postmenopausal women: the Women's Health Initiative Memory Study: a randomized controlled trial," JAMA 289:2651-2662 (2003).

Sicat, B.L. And Brokaw, D.K., "Nonhormonal alternatives for the treatment of hot flashes," Pharmacotherapy 24:79-93 (2004).

Simoni, D. et al., Novel combrestatin analogues awith antitumor activity, J. Med. Chem. 49:3143-3152 (2006).

Song, H.Z. et al., "In Vitro Study of the Chemopreventive Effects of Chinese Herbs against Hepatocarcinogenesis," J. Clin. Biochem. Nutri. 35:1-5 (2004).

Strom, A. et al., "Estrogen receptor beta inhibits 17beta-estradiol-stimulated proliferation of the breast cancer cell line. T47D," PNAS USA 101:1566-1571 (2004).

Suthar, A.C. et al., "Pharmacological activities of genistein an isoflavone from soy (Glycine max):Part II. Anti-cholesterol activity, effects on osteoporosis & menopausal symptoms," Indian J. Exp. Biol. 39(6):520-525 (2001).

Tagliaferri, M. et al., "A phase I trial of *Scutellaria barbata* (BZL101) for metastatic breast cancer," Abstract 1079, Breast Cancer Research and Treatment 94 (Suppl. 1): p. S66 2005.

Tan, B.K.H. et al., "Traditional Chinese Medicines in Breast Cancer: Clinical and Experimental Data," Abstract 356, Intl J Mol Med 12(Supp 1):S68 (2003).

Tee, M.K., "Estrogen Receptor Modulators Differentially Regulate Target Genes with Estrogen Receptors alpha and beta," Mol. Biol. Cell 15:1262-1272 (2004).

Tzagarakis-Foster, C. et al., "Estradiol represses human T-cell leukemia virus type 1 Tax activation of tumor necrosis factor-alpha gene transcription," J. Biol. Chem. 277:44772-44777 (2002).

Upchurch, D.M. et al., "Complementary and alternative medicine use among American women: fmdingf from the National Health Interview Survey, 2002, " J. Womens Health (Larchmt) 16:102-113 (2007).

Voskoglou-Nomikos et al., "Clinical Predictive Value of the in Vitro Cell Line, Human Xenograft, and Mouse Allograft Preclinical Cancer Models," Clin. Cancer Res. 9:4227-4239 (2003).

Wang, P. et al., "Mechanisms of Ageing and Development (2003);HDTIC-1 and HDTIC-2, two components extracted from Astragali Radix, delay replicative senescence of human diploid fiboblasts," Mechanisms of Aging and Dev. 124:1025-1034 (2003.

Wassertheil-Smoller, S. et al., "Effect of estrogen plus progestin on stroke in postmenopausal women: the Women's Health Initiative: a randomized trial," JAMA 28:2673-2684 (2003).

Wong, B.Y. et al., "Chinese Medicinal Herb *Scutellaria barbata* Modulates Apoptosis in TRAMP-C1 Prostate Cancer Cells and Tumor Development in TRAMP Mice," American Assoication for Cancer Research Conference on Frontiers in Cancer Prevention Research, Oct. 26-30, 2003, Phoenix, AZ, Cancer Epidemiology, Biomarkers & Prevention 12(Supp):1326s, Poster Session B, Nov. 2003, Poster B190.

Wong, B.Y. et al., "Modulation of Apoptosis and Cell Survival in Human Prostate Cancer Cells by the Chinese Medicinal Herb *Scutellaria barbata*," American Association for Cancer Research Conference on Frontiers in Cancer Prevention Research, Oct. 30-Nov. 2, 2005, Baltimore, MD Poster Session B, Biomarkers and Early Detection:Health Disparities, Cell,Molecular and Tumor Biology: Cell Death, Poster B21, p. 104.

Writing Group for the Women's Health Initiative Investigators, 2002, "Risks and benefits of estrogen plus progesin in healthy postmeopausal women: principal results," From the Women's Health Initiative randomized controlled trial, JAMA 288:321-333 (2002).

Xiao-fan, Z. et al., Chinese Medicine Teas:Simple, Proven Folk Formulas for Common Disease Promoting Health (Aug. 2004, Blue Poppy Press, Third Printing USA; pp. 122, 123, 252, 253-255 and 263.

Yin, X. et al., "Anticancer activity and mechanism of *Scutellaria barbata* extract on human lung cancer cell line A549," Life Sciences 75:2233-2244 (2004).

Yu, H. et al., "Anti-tumor effect of Chinese herbal medicines "*Scutellaria barbata* and Oldenlandia diffusa" on cancer cell lines and C3H-AVy mouse with spontaneous hepatocellular carcinoma," J Traditional Medicines 17(4):165-169 (2000).

Zhang, et al., "In Vitro Estrogenic Activities of Chinese Medicinal Plants Traditionally Used for the Management of Menopausal Symptoms," J. of Ethnopharmacology 98:3:295-300 (Apr. 2005).

Zhu, F. et al., "Regulative Effect of Traditional Chinese Medicine on Gene-expression Related to Precancerous Lesion of Gastric Cancer," Chinese J. Integrative Med. 11(1):76-80 (2005).

PCT/US05/44292 Search Report dated May 15, 2006.
PCT/US08/75493 Search Report dated Dec. 3, 2008.
PCT/US08/75405 Search Report dated Nov. 24, 2008.
PCT/US08/75499 Search Report dated Nov. 24, 2008.
PCT/US08/75468 Search Report dated Nov. 19, 2008.
PCT/US08/72651 Search Report dated Nov. 7, 2008.
PCT/US08/67495 Search Report dated Sep. 18, 2008.
PCT/US06/11862 Search Report dated Oct. 30, 2008.
PCT/US06/044224 Search Report dated Nov. 7, 2007.

Beliakoff et al., "Hormone-Refractory Breast Cancer Remains Sensitive to the Antitumor Activity of Heat Shock Protein 90 Inhibitors," Clinical Cancer Research 9:4961-4971 (2003).

Chunfeng et al., "RP-HPLC determination of *Scutellaria barbata* and other herbs in 4 main content of flavonoids," Chinese Pharmaceutical Journal, 2006,41 (17): 1342-1344.

Definition of *Scutellaria barbata* from Wikipedia, accessed on Dec. 28, 2009, pp. 1-2.

Fong et al., "Molecular mechanisms underlying selective cytotoxic activity of BZL101, an extract of *Scutellaria barbata,* towards breast cancer cells," Cancer Biology & Therapy 7(4):577-586 (2008).

Maggiolini et al., "The G Protein-coupled Receptor GPR30 Mediates c-fos Up-regulation by 17β-Estradiol and Phytoestrogens in Breast Cancer Cells," JBC 279:27008-27016 (2004).

Parl et al., "Prognostic Significance of Estrogen Receptor Status in Breast Cacner in Relation to Tumor Stage, Axillary Node Metastasis, and Histopathologic Grading," Cancer 54:2237-2242 (1984).

Wong et al., "Chinese Medicinal Herbs Modulate Mutagenesis, DNA Binding and Metabolism of Benzoaaupyrene," Phytotherapy Research 6(10:10-14 (1992).

Ye et al., "Anticancer activity of *Scutellaria baicalensis* and its potential mechanism," J. Alternative and Complementary Medicine 8(5):567-572 (2002).

Zips et al., "New anticancer agents in vitro and in vivo," In Vivo 19:1-7 (2005).

EP06837591 Search Report mailed Feb. 18, 2011.
PCT/US09/55945 IPRP mailed Mar. 17, 2011.

Boyce et al., "Src Inhibitors in Metastatic Bone Disease," Clin. Cancer Res. 12(20 Suppl.):6291 s-6295s (2006).

Camidge et al., "A first-in-man phase I tolerability and pharmacokinetic study of the cyclin-dependent kinase-inhibitor AZD5438 in healthy male volunteers," Cancer Chemother. Pharmacol. 60:391-398 (2007).

Centro Nacional De Investigaciones Oncologicas 2006, "CNIO Cancer Conference Medicinal Chemistry in Oncology," CNIO Cancer Conferences 2006:1-112.

Paez et al., "Response in Gefitinib Therapy," Science 304:1497-1500 (2004).

Rosano et al., "ZD4054, a Potent Endothelin Receptor A Antagonist, Inhibits Ovarian Carcinoma Cell Proliferation," Exp. Biol. Med. 231:1132-1135 (2006).

Ruff, "Targeted Therapy in Cancer in the 21$^{st}$ Century," CME 25(2):77-80 (2007).

Yeh et al., "Biological Characterization of ARRY-142886 (AZD6244), a Potent, Highly Selective Mitogen-Activated Protein Kinase 1/2/ Inhibitor," Clin. Cancer Res. 13(5):1576-1583 (2007).

PCT/US08/84082 Search Report dated Feb. 3, 2009.
PCT/US08/84085 Search Report dated Feb. 4, 2009.
PCT/US08/84087 Search Report dated Feb. 5, 2009.

* cited by examiner

Dose-response curves showing the response of several solid cancer tumor cells to BZL100.

Dose-response curves showing the response of breast solid cancer tumor cells to BZL101.

Dose-response curves comparing the response of breast solid cancer tumor cells and normal breast epithelium to BZL101.

Gel electrophoresis plate which demonstrates that nuclear DNA disintegration occurs during apoptosis of solid tumor cancer cells in contact with aqueous extracts of BZL101

BZL101 administered intraperitoneally (IP) reduces the growth of xenograft tumors in a mouse model.

- Day 0 – 10⁶ MCNeuA tumor cells, sc
- Herbs – 0.5 ml or 1.0 ml per mouse, i.p., every 2 days beginning day 0

The effect of the 821.101 administered by oral gavages and in interaction with cyclophosphamide administered in low dose in the drinking water on the tumors of mice in a xenograph model.

* Day 0 – 10⁶ tumor cells, sc
* CY – ~25 mg/kg/day, orally, beginning day 0
* Herb – 0.5 ml/mouse, every 3 days, beginning day 0

8-Oxo-guanine

PROCESS OF MAKING PURIFIED EXTRACT OF *SCUTELLARIA BARBATA* D. DON

CROSS-REFERENCE

This application claims benefit of priority under 35 U.S.C. §119(e) from provisional patent application 60/989,059, filed Nov. 19, 2007, which is incorporated herein by reference in its entirety.

BACKGROUND OF THE INVENTION

While advances in early detection and adjuvant therapy for breast cancer have had a favorable impact on patient survival in general, patients who develop advanced metastatic breast cancer are generally likely to face a less favorable prognosis. Commonly used hormonal and chemotherapeutic agents can lead to transient regression of tumors and can also palliate symptoms related to cancer. However, these treatments are often accompanied by toxicities and intolerable side effects and eventually become ineffective in controlling advanced stage breast cancer and its symptoms. Improvements in survival are modest, even with newer targeted biological agents. Moreover, in most metastatic cancers resistance to available conventional treatment ultimately develops or excessive side effects are seen with conventional therapies.

It is interesting to note that greater than 60% of all chemotherapeutic agents used in the treatment of breast cancer are derived from natural substances (Newman 2003). A fairly recent example is the development of taxanes from the Pacific yew tree, *Taxus brevifolia*. Throughout the world, it is estimated that approximately 80% of the world population still relies on botanical medicine as the primary source of therapy. In the West, botanical medicine is considered a popular form of complementary and alternative medicine among patients diagnosed with cancer. However, few clinical trials have been conducted to firmly assess the safety and efficacy of botanical agents for the treatment of breast cancer, despite anecdotal case reports of cures and clinical efficacy in women who have relied solely on botanical medicine for treatment. It has previously been shown that the aqueous extract of *Scutellaria barbata* can lead to growth inhibition of breast cancer cell lines in vitro ("Antiproliferative activity of Chinese medicinal herbs on breast cancer cells in vitro," Anticancer Res., 22(6C):3843-52 (2002)). BZL110, a concentrated aqueous extract of *Scutellaria Barbata*, was evaluated for antiproliferative activity on five breast cancer cell lines (SK-BR-3, $MCF_7$, MDA-MB-231, BT-474, and MCNeuA). These cell lines represent important prognostic phenotypes of breast cancer expressing a range of estrogen and HER2 receptors. BZL101, tested at a 1:10 dilution (15 µg/ml), demonstrated >50% growth inhibition on four of the five cell lines (Campbell, 2002). BZL101 showed >50% growth inhibition on a panel of lung, prostate and pancreatic cancer cell lines. BZL101 at the same dose did not cause >25% of growth inhibition on normal human mammary cells (HuMEC), demonstrating selectivity to cancer cells (Table 1). More so, BZL101 had a mild mitogenic effect on normal human lymphocytes. In cell cycle analysis, BZL101 caused an S phase burst and G1 arrest. BZL101 also attenuated mitochondrial membrane potential causing caspase-independent high molecular grade (HMG) apoptosis.

SUMMARY OF THE INVENTION

The inventor has noted that in a clinical trial of BZL101, some patients experienced gastrointestinal distress. While at the tested doses, the gastrointestinal distress did not rise to the level of a serious adverse event, it is at least conceivable that at higher doses the gastrointestinal distress could become dose-limiting, thereby limiting the maximal efficacy of treatment with the herb *Scutellaria barbata* D. Don (also referred to herein as "BZL," which is an abbreviation of the transliteration of its Chinese traditional name). The inventor has conceived that the gastrointestinal effects of BZL101 therapy could be attributable to inactive components (such as insoluble fiber) in the BZL101 "tea" administered to patients. It is the inventor's conception that a more purified version of the BZL extract would provide suitable, or even enhanced, anticancer efficacy, and an improved side effect profile, as compared to BZL101.

In some embodiments, the invention is a process for manufacturing a pharmaceutical extract of *Scutellaria barbata* D. Don, comprising: mixing *Scutellaria barbata* D. Don raw herb with water; heating the mixture; separating the liquid extract by filtration; concentrating the extract; filtering the concentrated extract; diluting the extract; freezing the diluted extract; drying the frozen extract; and milling the dried extract.

In some embodiments, the invention is a pharmaceutical composition for the treatment of cancer, comprising an extract of *Scutellaria barbata* D. Don, wherein the extract of *Scutellaria barbata* D. Don is manufactured according to the process comprising: mixing *Scutellaria barbata* D. Don raw herb with water; heating the mixture; separating the liquid extract by filtration; concentrating the extract; filtering the concentrated extract; diluting the extract; freezing the diluted extract; drying the frozen extract; and milling the dried extract.

In some embodiments, the invention is a method of treating cancer in a patient, comprising administering to the patient an effective amount of an extract of *Scutellaria barbata* D. Don, wherein the extract is manufactured by the process comprising: mixing *Scutellaria barbata* D. Don raw herb with water; heating the mixture; separating the liquid extract by filtration; concentrating the extract; filtering the concentrated extract; diluting the extract; freezing the diluted extract; drying the frozen extract; and milling the dried extract.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
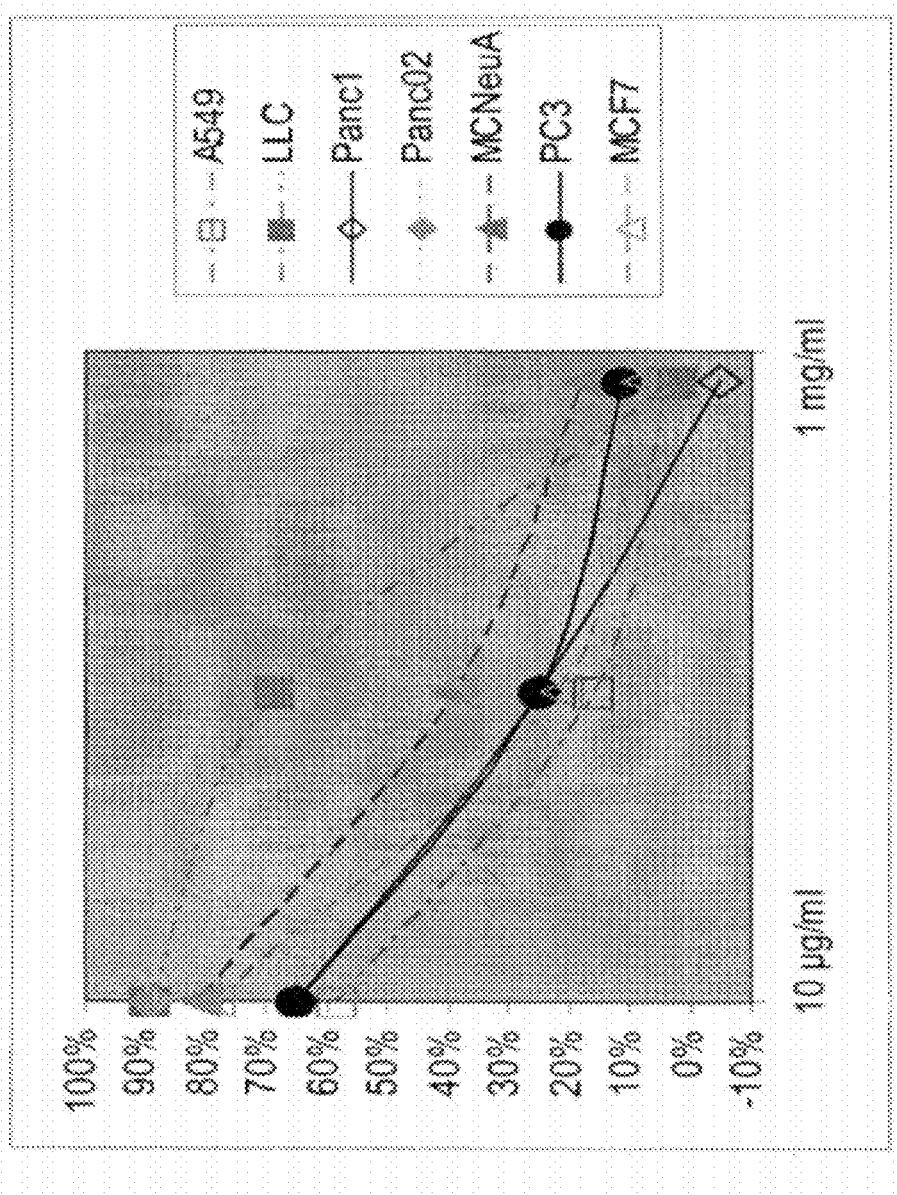
FIG. 1 shows dose-response curves showing the response of several solid cancer tumor cells to aqueous extract of the herb of this invention.

As used herein, the indefinite article "a" or "an" is to be interpreted as meaning "at least one" unless further qualified. The conjunction "or" is, unless otherwise qualified, intended to be inclusive.

Process of Purifying an Extract of *Scutellaria Barbata* D. Don

In some embodiments, the invention is a process for manufacturing a pharmaceutical extract of *Scutellaria barbata* D. Don, comprising: mixing *Scutellaria barbata* D. Don raw herb with water; heating the mixture; separating the liquid extract by filtration; concentrating the extract; filtering the concentrated extract; diluting the extract; freezing the diluted extract; drying the frozen extract; and milling the dried extract.

In some embodiments, the amount of *Scutellaria barbata* D. Don mixed with deionized water is in a ratio of 1:10. In some embodiments, the amount of *Scutellaria barbata* D. Don is about 300 kg to about 3000 kg.

In some embodiments, the mixture is heated to about 100 C. In some embodiments, the temperature of the mixture is reduced to about 70 C to about 75 C. In some embodiments, the temperature is maintained for about an hour. In some embodiments, the liquid extract is separated using a 80 mesh (177 um) screen.

In some embodiments, the liquid extract is concentrated by evaporation. In some embodiments, the liquid extract is concentrated by evaporation at a temperature from about 40 C to about 60 C. In some embodiments, the concentrated extract is filtered using a 325 mesh (44 um) screen.

In some embodiments, the filtered concentrated extract is diluted with purified water. In some embodiments, the filtered concentrated extract is diluted 3 fold.

In some embodiments, the diluted extract is frozen using on freeze drier poly-lined trays.

In some embodiments, the invention is a pharmaceutical composition for the treatment of cancer, comprising an extract of *Scutellaria barbata* D. Don, wherein the extract of *Scutellaria barbata* D. Don is manufactured according to the process comprising: mixing *Scutellaria barbata* D. Don raw herb with water; heating the mixture; separating the liquid extract by filtration; concentrating the extract; filtering the concentrated extract; diluting the extract; freezing the diluted extract; drying the frozen extract; and milling the dried extract.

In some embodiments, the amount of *Scutellaria barbata* D. Don mixed with deionized water is in a ratio of 11:10. In some embodiments, the amount of *Scutellaria barbata* D. Don is about 300 kg to about 3000 kg.

In some embodiments, the mixture is heated to about 100 C. In some embodiments, the temperature of the mixture is reduced to about 70 C to about 75 C. In some embodiments, the temperature is maintained for about an hour. In some embodiments, the liquid extract is separated using a 80 mesh (177 um) screen.

In some embodiments, the liquid extract is concentrated by evaporation. In some embodiments, the liquid extract is concentrated by evaporation at a temperature from about 40 C to about 60 C. In some embodiments, the concentrated extract is filtered using a 325 mesh (44 um) screen.

In some embodiments, the filtered concentrated extract is diluted with purified water. In some embodiments, the filtered concentrated extract is diluted 3 fold.

In some embodiments, the diluted extract is frozen using on freeze drier poly-lined trays.

In some embodiments, the composition further comprises at least one additional ingredient selected from the group consisting of: active pharmaceutical ingredients; enhancers; excipients; and agents used to adjust the pH, buffer the composition, prevent degradation, and improve taste, appearance, or odor.

In some embodiments, the invention is a method of treating cancer in a patient comprising administering to the patient an effective amount of an extract of *Scutellaria barbata* D. Don, wherein the extract is manufactured by the process comprising: mixing *Scutellaria barbata* D. Don raw herb with water; heating the mixture; separating the liquid extract by filtration; concentrating the extract; filtering the concentrated extract; diluting the extract; freezing the diluted extract; drying the frozen extract; and milling the dried extract.

In some embodiments, the amount of *Scutellaria barbata* D. Don mixed with deionized water is in a ratio of 1:10. In some embodiments, the amount of *Scutellaria barbata* D. Don is about 300 kg to about 3000 kg.

In some embodiments, the mixture is heated to about 100 C. In some embodiments, the temperature of the mixture is reduced to about 70 C to about 75 C. In some embodiments, the temperature is maintained for about an hour. In some embodiments, the liquid extract is separated using a 80 mesh (177 um) screen.

In some embodiments, the liquid extract is concentrated by evaporation. In some embodiments, the liquid extract is concentrated by evaporation at a temperature from about 40 C to about 60 C. In some embodiments, the concentrated extract is filtered using a 325 mesh (44 um) screen.

In some embodiments, the filtered concentrated extract is diluted with purified water. In some embodiments, the filtered concentrated extract is diluted 3 fold.

In some embodiments, the diluted extract is frozen using on freeze drier poly-lined trays.

In some embodiments, the cancer is a breast cancer. In some embodiments, the breast cancer expresses nuclear estrogen receptor at a level that does not exceed a predetermined threshold. In some embodiments, the breast cancer expresses nuclear estrogen receptor at a level that exceeds a predetermined threshold.

In some embodiments, the effective amount of extract of *Scutellaria barbata* D. Don consists essentially of the soluble dry solid portion of from about 1 to about 20,000 g of *Scutellaria barbata* D. Don. In some embodiments, the effective amount of extract of *Scutellaria barhata* D. Don consists essentially of the soluble dry solid portion of from about 10 to about 10,000 g of *Scutellaria barbara* D. Don. In some embodiments, the effective amount of extract of *Scutellaria barbata* D. Don consists essentially of the soluble dry solid portion of from about 50 to about 5,000 g of *Scutellaria barbara* D. Don. In some embodiments, the effective amount of extract of *Scutellaria barbara* D. Don consists essentially of the soluble dry solid portion of from about 100 to about 2,500 g of *Scutellaria barbata* D. Don. In some embodiments, the effective amount of extract of *Scutellaria barbata* D. Don consists essentially of the soluble dry solid portion of from about 300 to about 5,000 g of *Scutellaria barbata* D. Don. In some embodiments, the effective amount of extract of *Scutellaria barbata* D. Don consists essentially of the soluble dry solid portion of from about 500 to about 5,000 g of *Scutellaria barbata* D. Don. In some embodiments, the effective amount of extract of *Scutellaria barbata* D. Don consists essentially of the soluble dry solid portion of from about 800 to about 5,000 g of *Scutellaria barbata* D. Don. In some embodiments, the effective amount of extract of *Scutellaria barbata* D. Don consists essentially of the soluble dry solid portion of from about 300 to about 10,000 g of *Scutellaria barbata* D. Don. In some embodiments, the effective amount of extract of *Scutellaria barbata* D. Don consists essentially of the soluble dry solid portion of from about 500 to about 10,000 g of *Scutellaria barbata* D. Don. In some embodiments, the effective amount of extract of *Scutellaria barbata* D. Don consists essentially of the soluble dry solid portion of from about 800 to about 10,000 g of *Scutellaria barbata* D. Don. In some embodiments, the effective amount of extract of *Scutellaria barbara* D. Don consists essentially of the soluble dry solid portion of from about 800 to about 10,000 g of *Scutellaria barbata* D. Don. In some embodiments, the effective amount of extract of *Scutellaria barbata* D. Don consists essentially of the soluble dry solid portion of from about 800 to about 20,000 g of *Scutellaria barbata* D. Don. In some embodiments, the effective amount of extract of *Scutellaria barbata* D. Don consists essentially of the soluble dry solid portion of from about 1200 to about 20,000 g of *Scutellaria barbara* D. Don. In some embodiments, the effective amount of extract of *Scutellaria barbata* D. Don consists essentially of the soluble dry solid portion of from about 2400 to about 10,000 g of *Scutellaria barbata* D. Don.

*Scutellaria Barbara* D. Don (BZL)

*Scutellaria barbata* extract, when placed in contact with solid tumor cancer cells, inhibits the activity, alternatively—the growth and/or proliferation, of the cells. The herb is selected from the species *Scutellaria barbata* D. Don of the Lamiaceae Family. In Chinese it is called Ban Zhi Lian (BZL). It grows mainly in areas southeastern of the Yellow River (Huang Po) in the provinces of Sichuan, Jiangsu, Jiangxi, Fujian, Guangdong, Guangxi and Shaanxi, but not exclusively. The plant is harvested in late summer and early autumn after it blooms (May-June). The aerial part is cut from the root. Only the aerial part (leaves and stems) is used for preparation of the extract of *Scutellaria barbata* D. Don, as described herein. The herb is dried in the sun and packed as a whole plant. The herb is received with no separation between leaves and stems.

Thus, except as otherwise specifically qualified herein, the term "extract" refers to an extract of the aerial portion (leaves and stems) of *Scutellaria barbata* D. Don. Except as otherwise specifically qualified herein, the term "herb" refers to the aerial portion of *Scutellaria barbata* D. Don, Except as otherwise specifically qualified herein the term "a pharmaceutically effective amount" of extract means an amount of extract sufficient to bring about a positive clinical outcome in at least one patient. A positive clinical outcome will be measured by conventional clinical standards know to the skilled oncologist. Some suitable positive clinical outcomes include partial remission, complete remission, a reduction in tumor size, stable tumor size, prevention of metastasis for a period exceeding at least about 3 months, at least about 6 months, at least about 9 months or at least about 12 months, extension of expected life expectancy, prevention of recurrence of a cancer, extension of the expected time necessary for recurrence of cancer. It is expected that an aspect of the invention will be that when the extract is administered in conjunction with another chemotherapeutic agent, the amount of extract that will be necessary to achieve a positive clinical outcome—and thus the pharmaceutically effective amount—will be less than that necessary when the extract is used as a single entity agent. A process of manufacturing a dose of extract is set forth in detail below. For purposes of this disclosure, the pharmaceutically effective amount of extract will be the dry solid portion of a hot water or ethanolic extract from approximately 1-20, 000 g of *Scutellaria barbata* D. Don. In some embodiments, the pharmaceutically effective dose will be the dry solid portion of a hot aqueous or ethanolic extract of about 10 to about 2000 g of *Scutellaria barbata* D. Don.

As is described in the Detailed Description section, below, the herb is substantially more active in inhibiting the activity of different types of cancer cells. It is therefore a presently preferred aspect of this invention that the herbal extract obtained from the species *Scutellaria barbara*. It is a particularly presently preferred aspect of this invention that the herbal extract is obtained from *Scutellaria barbata* D. Don.

It has been previously shown that an extract of *Scutellaria barbata* D. Don. inhibits solid tumors in vitro. Some solid tumor cancer cell lines in which the extract is active include: SKBR3 cell, a MCF7 cell, a MDA-MB231 cell, a BT474 cell or a MCNeuA cell (breast cancer cells), A549 cell, LLC cell (Lung Cancer cells), Panc1 cells, Panc02 cells (Pancreatic cancer cells), PC-3 cells LNCaP cells (Prostate Cancer cells), OVCAR cells, SKOV3 cells (Ovarian Cancer cells).

Table 1 contains a description of the herb, from which extracts are obtained, listed by family, genus, species and traditional Chinese name.

TABLE 1

| Family | genus | Species | Chinese name | Herb part |
|---|---|---|---|---|
| Lamiaceae | Scutellaria | Barbata D. Don | Ban Zhi Lian | aerial |

Table 2A shows the degree of inhibition of the activity of several in vitro solid breast cancer tumor cell lines by the extract.

TABLE 2A

| MCF7 | SKBR3 | MDA-MB231 | BT474 | MCNeuA |
|---|---|---|---|---|
| ++ | ++ | ++ | + | ++ |

Table 2B shows the degree of inhibition of the activity of several in vitro solid cancer tumor cell lines by the extract.

TABLE 2B

| Lung Cancer | | Pancreatic Cancer | | Prostate Cancer | | Breast Cancer | | |
|---|---|---|---|---|---|---|---|---|
| A549 | LLC | Panel | Panc02 | PC-3 | LNCaP | MCF7 | MCNeuA | Breast Normal HuMEC |
| + | ++ | + | ++ | + | + | ++ | ++ | − |
| 1424 | 492 | 1054 | 594 | 1035 | 1516 | 818 | 619 | |

− <50% inhibition, + 51-75% inhibition, ++ >75% inhibition, $IC_{50}$ values (μg/ml)

The active ingredients in the extract are not known. The extract loses activity when reconstituted after drying, as well as when the extract is separated through physical and chemical means. The known chemical ingredients in the plant are scutellarin, scutelarein, carthamidin, isocarthamidin and wagonin.

An extract comprises residue of soluble solids obtained after the herb is for example, without limitation, chopped, crushed, pulverized, minced or otherwise treated to increase the effective surface area of the surface area of the herb and is placed in intimate contact with a liquid, usually, but not necessarily, under conditions of agitation and elevated temperature. Then, after a period of time under the foregoing conditions the mixture is filtered to remove a substantial portion of insoluble solids and the liquid is removed by, for example but not limitation, evaporation or freeze drying to produce the aforementioned residue. This residue contains soluble solids, which are believed to comprise the active agent in the extract and in some cases optionally a portion of insoluble solids that were not removed by previous filtration. The liquid used to obtain an extract may be water or an organic solvent, for example, without limitation, an alcohol such as methyl, ethyl or isopropyl alcohol, a ketone such as acetone or methyl ethyl ketone (MEK), an ester such as ethyl acetate, an organochlorine compound such as methylene chloride, chloroform or carbon tetrachloride, a hydrocarbon such as pentane, hexane or benzene and the like. An extract may also be obtained by using a combination of these solvents with or without water.

As used herein, "administer", "administering" or "administration" refers to the delivery of an extract or of a pharmaceutical composition containing an extract to a patient.

A "patient" refers to any higher organism that is susceptible to solid tumor cancers. Examples of such higher organisms include, without limitation, mice, rats, rabbits, dogs, cats, horses, cows, pigs, sheep, fish and reptiles. In currently preferred embodiments, the term "patient" refers to a human being.

As used herein, the term "therapeutically effective amount" refers to that amount of an extract or combination of extracts of this invention which has the effect of (1) reducing the size of the tumor; (2) inhibiting (that is, slowing to some extent, preferably stopping) tumor metastasis; (3) inhibiting to some extent (that is slowing to some extent, preferably stopping) tumor growth; and/or, (4) relieving to some extent (or preferably eliminating) one or more symptoms associated with cancer (5) stabilizing the growth of the tumor, (6) extending the time to disease progression, (7) improving overall survival.

As used herein, a "pharmaceutical composition" refers to a mixture of an extract described herein with another component or components, such as physiologically acceptable carriers and excipients. The purpose of a pharmacological composition is to facilitate administration of an extract or extracts of this invention to patient. In some currently preferred embodiments, the pharmaceutical composition can include water. In some currently preferred embodiments, the pharmaceutical composition can additionally include a flavor-masking agent.

As used herein, the term "pharmaceutically acceptable" means that the modified agent or excipient is generally regarded as acceptable for use in a pharmaceutical composition.

As used herein, a "physiologically acceptable carrier" refers to a carrier or diluent that does not cause significant irritation to an organism and does not abrogate the biological activity and properties of the administered composition.

As used herein, an "excipient" refers to an inert substance added to a pharmaceutical composition to further facilitate administration of an extract or extracts of this invention. Examples, without limitation, of excipients include calcium carbonate, calcium phosphate, various sugars and types of starch, cellulose derivatives, gelatin, vegetable oils and polyethylene glycols.

At one time, botanical agents were the most significant group of substances used by healers to treat patients. According to a WHO survey, 80% of the world's population still relies heavily on herbal medicine as their primary source of therapy. In Western culture one-quarter of the active components of currently prescribed drugs were first identified in plants and over half of the 50 most popular drugs today are derived from plant materials. In addition, over 60% of chemotherapeutic agents used in the treatment of cancer are derived from natural substances.

A useful strategy for the discovery of biologically active compounds from plants is the ethno-pharmacological approach which uses information about traditional medicinal uses of plants. The long history of a plant's use in treating a disorder, regardless of whether the disorder is well-characterized, e.g., skin rash, or is rather more nebulous, e.g., hot blood, is a clear indicator that something in the plant has some manner of beneficial effect on a disorder, otherwise the use of the plant would have faded in time. Furthermore, the fact that homeopathic practitioners have been administering the plant or an extract thereof to human patients for, often, centuries provides a compelling argument for the safety of the plant or its extracts in human beings.

Such alternative approaches to medicine are becoming more and more widely accepted and used in the United States as well to treat a broad spectrum of conditions as well as to maintain wellness. It is estimated that one in two Americans currently uses alternative therapies at one time or another. In particular, the most popular complementary or fully alternative approach to the treatment of their cancers by patients is botanical agents/herbal medicines.

Traditional Chinese medicine (TCM) is often the treatment modality of choice by cancer patients opting for an alternative approach to dealing with their ailment. Patients use TCM both as anti-cancer agents and to alleviate the side effects of standard chemotherapy. However, TCM lacks the scientifically sound methodology required of Western pharmacology and the use of TCM is often hit or miss in its effectiveness. There remains a need for the discovery of specific herbal extracts and combinations thereof that have a specific utility and for which there is scientific evidence as to why they work in that use. This invention provides such extract and compositions decoction.

Pharmaceutical Compositions and Modes of Administrations

An extract of this invention can be administered to a patient either as a "tea," without combination with any other substances or further manipulation, or it can be administered as a pharmaceutical composition where the extract is mixed with suitable carriers or recipient(s). In treating a patient exhibiting a disorder of interest, a therapeutically effective amount of the extract is administered. A therapeutically effective amount refers to that amount of the extract that results in amelioration of symptoms or a prolongation of survival in a patient, and may include destruction of a malignant tumor of a microbial infection.

When administered without combination with any other substances, the composition comprising extract of *Scutellaria Barbara* (especially *Scutellaria Barbata* D. Don) may be encased in a suitable capsule, such as a gelatin capsule. When administered in admixture with other excipients, adjuvants, binders, diluents, disintegrants, etc., the dry extract of *Scurellaria Barbata* may be compressed into a capsule or caplet in a conventional manner that is well-known in the art.

Toxicity and therapeutic efficacy of the extracts, i.e., determining the LD50 (the dose lethal to 50% of the population) and the ED50 (the dose therapeutically effective in 50% of the population) can be determined by standard pharmaceutical procedures in cell cultures or experimental animals. The dose ratio between toxic and therapeutic effects is the therapeutic index and it can be expressed as the ratio LD50/ED50. Extracts that exhibit large therapeutic indices are preferred. The data obtained from these cell culture assays and animal studies can be used in formulating a range of dosages for use in humans, in particular for internal use, that include ED50 with little or no toxicity. The dosage may vary within this range depending upon the dosage form employed and the route of administration utilized. In general, since the extracts used in the methods of this invention have been used in TCM, they are known to be relatively non-toxic to humans and therefore it is expected that they will exhibit large therapeutic indices.

For any extract used in the method of invention, the therapeutically effective dose can be estimated initially from cell culture assays. For example, a dose can be formulated in animal models to achieve a circulating plasma concentration range that includes the IC50 as determined in cell culture. Such information can be used to more accurately determine useful doses in humans. Levels in plasma may be measured, for example, by HPLC.

The exact formulation, route of administration and dosage can be chosen by the individual physician in view of the patient's condition and based on knowledge of TCM. (See e.g. Fingl et al., in The Pharmacological Basis of Therapeutics, 1975, Ch. 1, p. 1). It should be noted that the attending physician would know how and when to terminate, interrupt, or adjust administration due to toxicity, or organ dysfunction. Conversely, the attending physician would also know to adjust treatment to higher levels if the clinical response is not adequate. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

If desired, standard western medicine techniques for formulation and administration may be used, such as those found in *Remington's Pharmaceutical Sciences*, $18^{th}$ ed., Mack Publishing Co., Easton, Pa. (1990). Suitable routes may include: oral, rectal, transdermal, vaginal, transmucosal, or intestinal administration; parenteral delivery, including intramuscular, subcutaneous, intramedullary injections; as well as intrathecal, direct intraventricular, intravenous, intraperitoneal, intranasal, or intraocular injections, to name a just a few. In particular embodiments, the extract of the invention is administered orally.

For injection, an extract of this invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate an extract herein use in the methods disclosed for the practice of this invention in dosages suitable for systemic administration is within the scope of the invention. With proper choice of carrier and suitable manufacturing practice, an extract of the present invention, in particular those formulated as solutions, may be administered parenterally, such as by intravenous injection. Likewise, an extract can be formulated, using pharmaceutically acceptable carriers well known in the art, into dosages suitable for oral administration. Such carriers enable extracts to be formulated as tablets, pills, capsules, liquids, gels, syrups, slurries, suspensions and the like, for oral ingestion by a patient to be treated.

Pharmaceutical compositions suitable for use in the present invention are compositions wherein an extract is contained in an effective amount to achieve its intended purpose. Determination of the effective amount is well within the capability of those skilled in the art, especially in light of the detailed disclosure provided herein. A pharmaceutical composition may contain suitable pharmaceutically acceptable carriers including excipients and auxiliaries that facilitate processing of the extracts into preparations that can be used pharmaceutically. The preparations formulated for oral administration may be in the form of tablets, dragees, capsules, or solutions. The pharmaceutical compositions of the present invention may be manufactured in a manner that is itself known, e.g., by means of convention mixing, dissolving, granulating, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutically formulations for parenteral administration include aqueous solutions of an extract in water-soluble form. Additionally, suspensions of an extract may be prepared as appropriate oily injection suspensions may contain substances that increase the viscosity of the suspension, such as sodium carboxymethyl cellulose, sorbitol, or dextran. Optionally, the suspension may also contain suitable stabilizers or agents that increase the solubility of an extract to allow for the preparation of highly concentrated solutions.

Pharmaceutical preparations for oral use can be obtained by combining an extract with solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum Arabic, talc, polyvinyl pyrrolidone, carpool gel, polyethylene glycol, and/or titanium dioxide, lacquer solutions, and suitable organic solvents or solvent mixtures. Dyestuffs or pigments may be added to the tablets or dragee coatings for identification or to characterize different combinations of extracts and/or doses.

Pharmaceutical preparations that can be used orally include push-fit capsules made of gelatin, as well as soft, sealed capsules made of gelatin and a plasticizer, such as glycerol or sorbitol. The push-fit capsules contain the extract in admixture with fillers such as lactose, binders such as starches, and/or lubricants such as talc or magnesium separate and, optionally, stabilizers. In soft capsules, the extract may be dissolved or suspended in suitable liquids, such as fatty oils, liquid paraffin, or liquid polyethylene glycols.

The dosage of extract of *Scutellaria barbata* D. Don will vary depending upon the tumor type, the stage of disease, the species of patient and the individual patient. In some embodiments, the amount of extract of *Scutellaria barbata* D. Don (BZL) administered to a human patient will be the dry solid residue extracted from about 0.1 g to about 20,000 g of dried solid plant parts of BZL. In some embodiments, the effective dose is the dry solid residue extracted from about 1 to about 1000 g of BZL. In some embodiments, the effective dose will be the dry solid residue extracted from about 10 to about 800 g of BZL.

EXAMPLES

The herbs, from which the extracts of this invention were obtained, were purchased from Shen Nong Herbs, Berkeley, Calif. Their identity was confirmed by reference to traditional pharmaceutical literature.

Comparative Preparative Example 1

Preparation of BZL101 for In Vitro and Mouse Experiments

Herbal extract was prepared as "boiled teas", which is how most are prepared for use in traditional treatment regimes. Aqueous extracts were prepared by adding 7.5 g of dry ground herb to 125 ml distilled water, bringing the mixture to a boil and then simmering for 45 minutes. The mixture was cooled, during which period most of the solids sank to the bottom of the vessel. The aqueous layer was carefully decanted off of the residual solids, centrifuged for 5 minutes at 1500 rpm, sterile filtered through a 0.45 µm filter and stored at 4° C. until used. Generally, the extracts were tested within 1-2 weeks of preparation although most of the active extracts were found to retain activity after storage at 4° C. for several additional weeks. An aliquot of each extract was dried under vacuum and the dry weight of the water soluble substances extracted from each herb determined.

Comparative Preparative Example 2

Preparation of BZL101 for Human In Vivo Experiments

BZL101 is an aqueous extract of the aerial part of *Scutellaria Barbata* D. Don of the Lamiaceae family. Herba *Scutellaria barbata* D. Don (Chinese pin yin transliteration—Ban Zhi Lian (BZL)) is grown mainly in areas southeastern of the Yellow River (Huang Po) in the provinces of Sichuan, Jiangsu, Jiangxi, Fujian, Guangdong, Guangxi and Shaanxi. The plant is harvested in late summer and early autumn after it blooms. The aerial part (leaves and stems) is cut from the root and is used as starting material (BZL). The aerial part of the herb is dried in the sun, packed as a whole plant. The herb is identified and verified through botanical, morphological and chemical characteristics to ensure purity.

A single dose of BZL 101 is made through the following procedure and is termed BZL101 (BioNovo, Inc., Emeryville, Calif.).

- 180 grams of the raw herb is ground to fine powder (25 mesh)
- The powder is mixed with 1800 ml of distilled water to form a slurry
- The slurry is than simmered at 70-72° C. for 60 minutes
- The extract is decanted and filtered through 22 µm filter
- The supernatant weight after extraction is 168 gm
- The volume of the solution is 1750 ml
- The extract is concentrated with a vacuum evaporator to reduce the volume of water to 350 ml which constitutes a 5:1 concentration of the original solution
- The dry weight of soluble material in the extract is 12 gm
- It is packaged in a sterile, vacuum sealed container
- Testing for bacteria, yeast and heavy metals are preformed by an accredited laboratory Comparative Example 1

In Vitro Inhibition of Cancer Cell Activity Cell Lines and Culture

The extract obtained in Preparative Example 1, above, was tested against four human breast cancer cell lines, SKBR3, MFC-7, MDA-MB231 and BT474, and one murine breast cancer cell line, MCNeuA. All lines were maintained in 90% DME supplement with 2.0 mom L-glutamine, 100 IU/ml penicillin, 100 µg/ml streptomycin and 10% heat-inactivated fetal bovine serum. Cells at 70-80% confluence were used for plating for growth inhibition assays.

Figure 2:
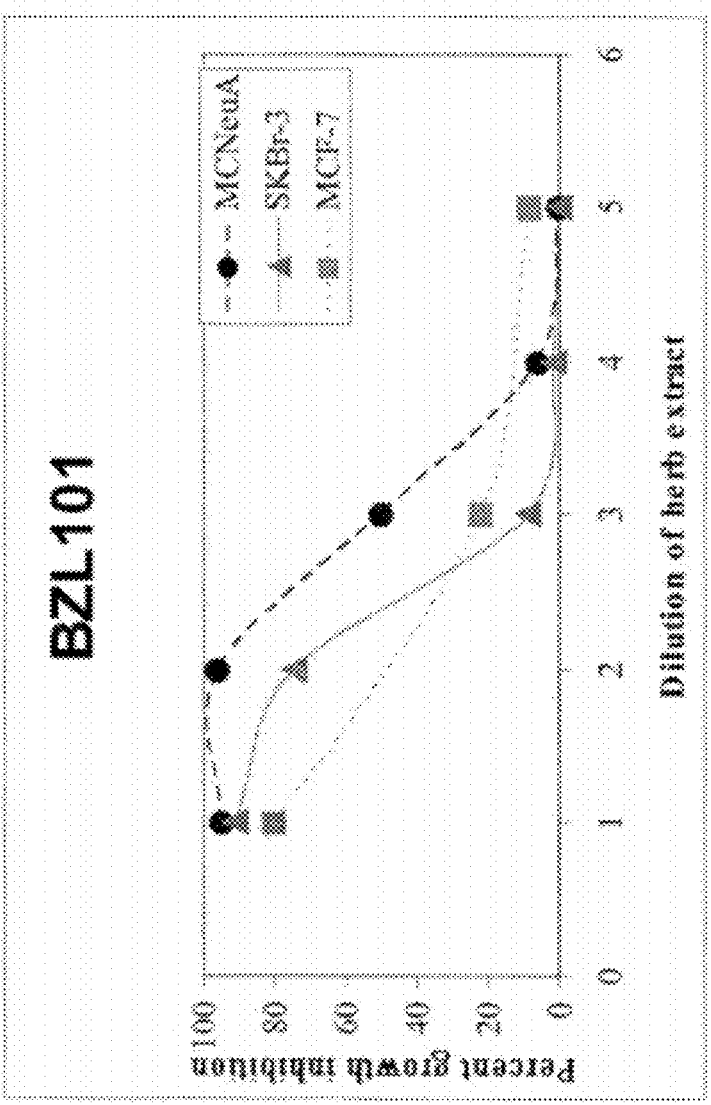
FIG. 2 shows dose-response curves showing the response of several breast solid cancer tumor cells to aqueous extract of the herb of the invention.
Figure 3:
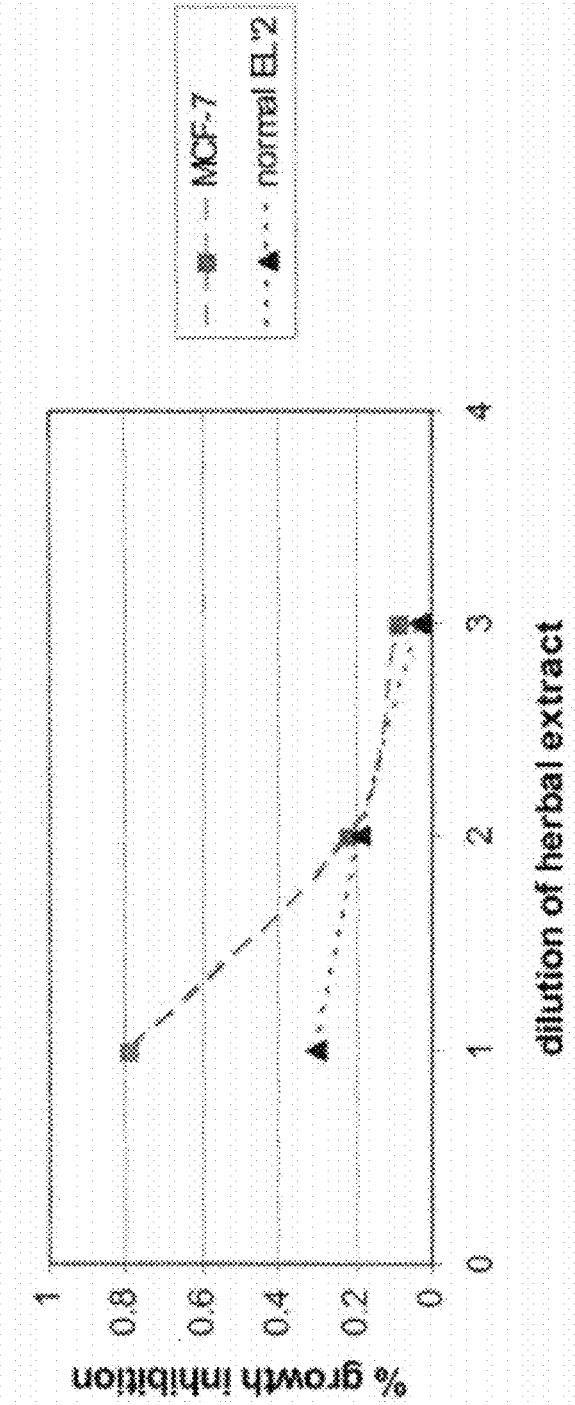
FIG. 3 shows dose-response curves comparing the response of breast solid cancer tumor cells and normal breast epithelium to aqueous extract of the herb of this invention.
Figure 4:
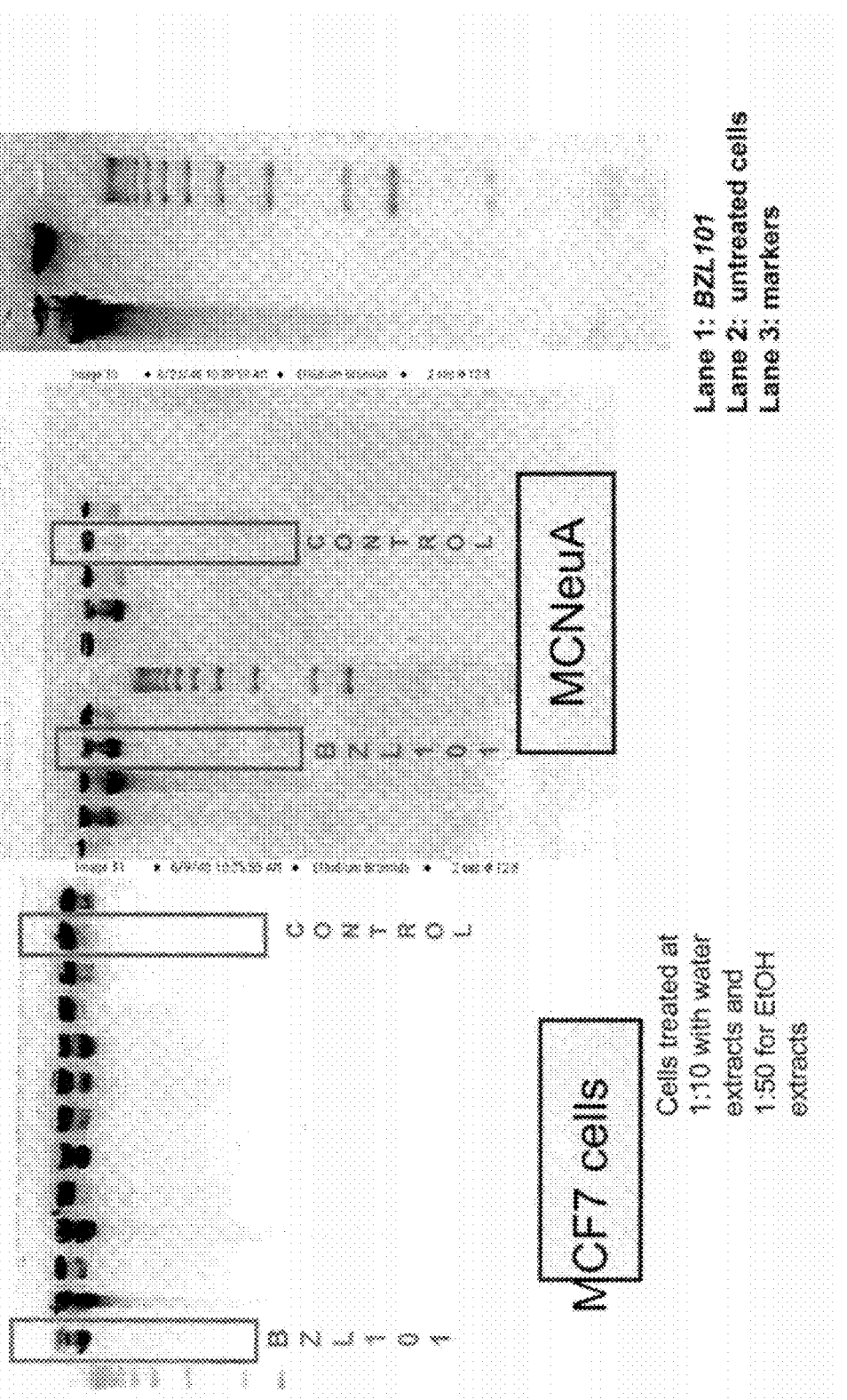
FIG. 4 shows gel electrophoresis plate, which demonstrates that nuclear DNA disintegration occurs during apoptosis of solid tumor cancer cells in contact with aqueous extracts of the herb of this invention.

Cells were plated in 96-well flat bottom plates at 5,000 to 10,000 cells/well. The difference in number of cells plated adjusts for differences in the growth rates of these cell lines. Cells were allowed to adhere to the well walls overnight; then the extracts were added to triplicate wells at a 1:10 final dilution in culture medium for initial screening. For generating dose-response curves, serial 3-fold dilutions, starting at 1:10 dilution over 6 rows of wells were used. Water was added to the control wells at 1:10 dilution in culture medium. The plates were incubated at 37° C., 5% $CO_2$, for 3 days and then assayed for growth inhibition using a crystal violet assay (Bernhardt, G., et al., *Standardized Kinetic Microassay to Quantify Differential Chemosensitivity on the Basis of Proliferative Activity*, 1992, J. Cancer Res. Clin. Oncol., 118:35-43). Cells remaining adherent to the well walls were rinsed with PBS, the fixed cells were stained with 0.02% aqueous crystal violet (50 μl/well) for 30 minutes after which the wells were washed thoroughly with distilled water. The crystal violet stain bound by the cells was solubilized in 79% ethanol (100 μl/well) and the plates analyzed on a microplate reader (Molecular Devices) ay 595 nm. The percent inhibition was calculated as the average optical density of the control wells minus average optical density extract well divided by the average optical density of the control wells. Dose-response curves on SKBR3, MCF7 and MCNeuA cells for several of the extracts are shown in FIGS. 1-3. As can be seen, the concentration at which the extracts inhibited the activity of the cells by 50% (the IC50) ranged from over 1 mg/ml down to about 10 μg/ml.

ethidium bromide and photographed under UV transillumination to give intense images. The images obtained are shown in FIG. 4.

Figure 7:
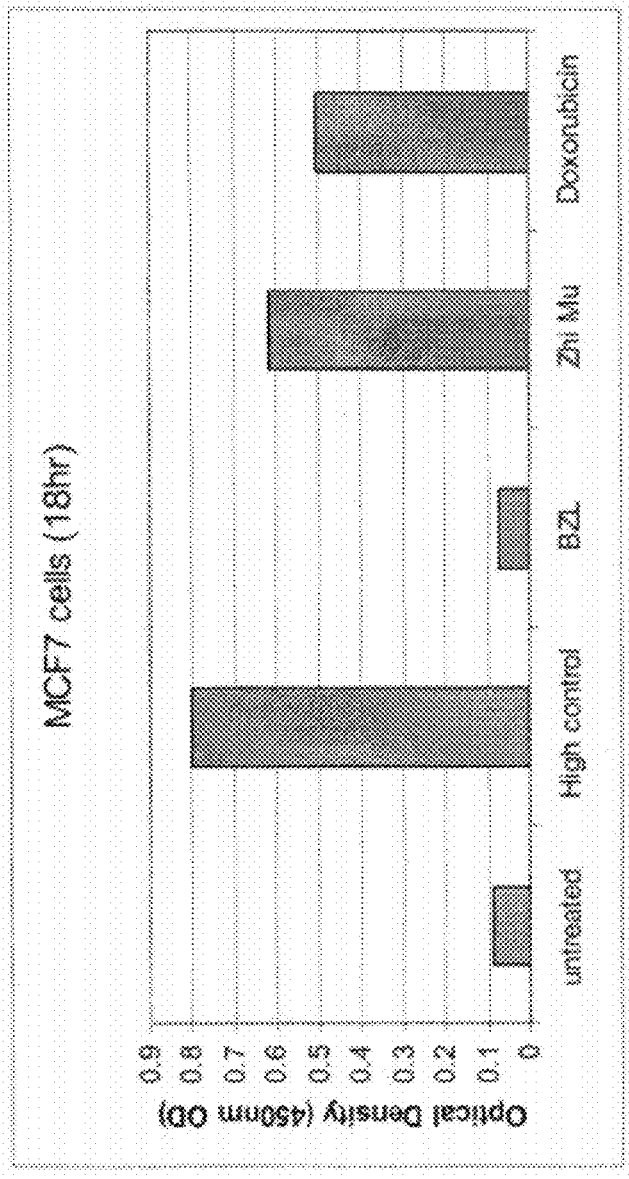
FIG. 7 shows that the herb extract induces apoptosis without activating caspases.
Figure 8:
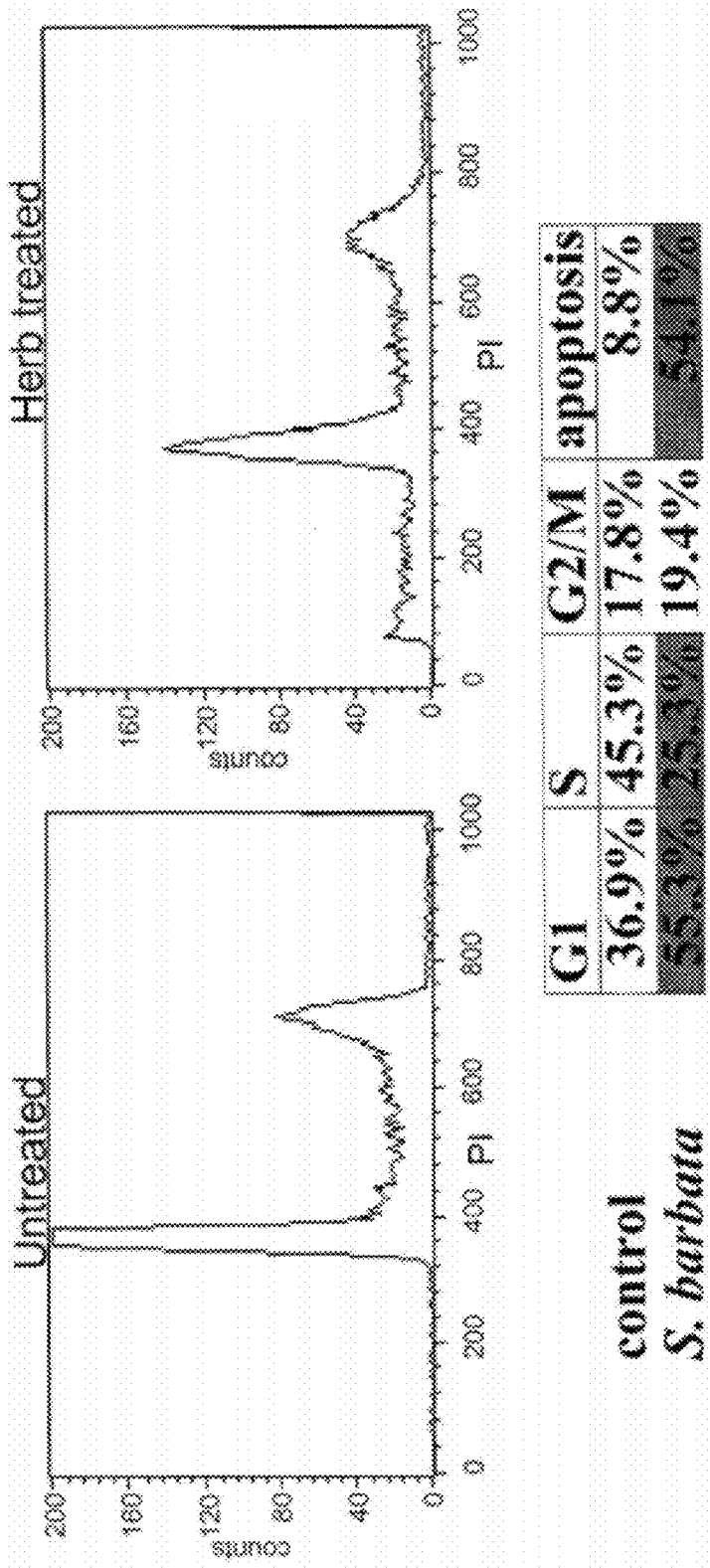
FIG. 8 shows that the herb extract in cell cycle analysis arrests the cells at the G1 phase.
Figure 9:
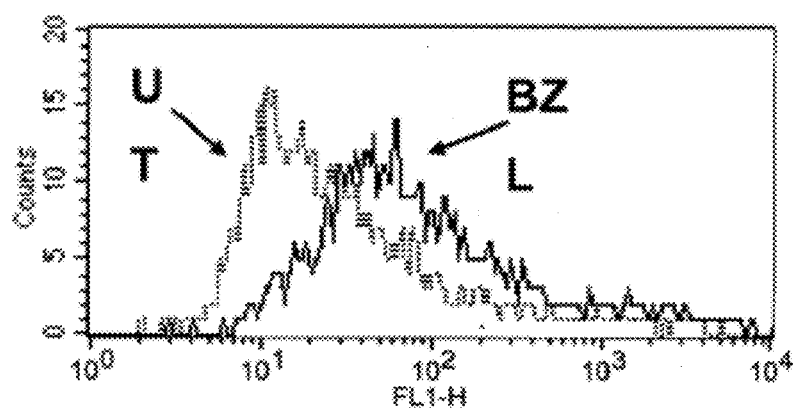
FIG. 9 shows that illustrates that BZL101 leads to oxidative DNA damage. Formation of 8-oxoguanine, the most ubiquitous marker of DNA oxidation, was quantified through flow cytometric analysis of fixed permeabilzed cells incubated with avidin fluorescein, that was shown to bind relatively specifically to 8-oxoguanine. There is a clear increase in binding of avidin to BZL101 treated SKBr3 cells versus untreated cells.
Figure 10:
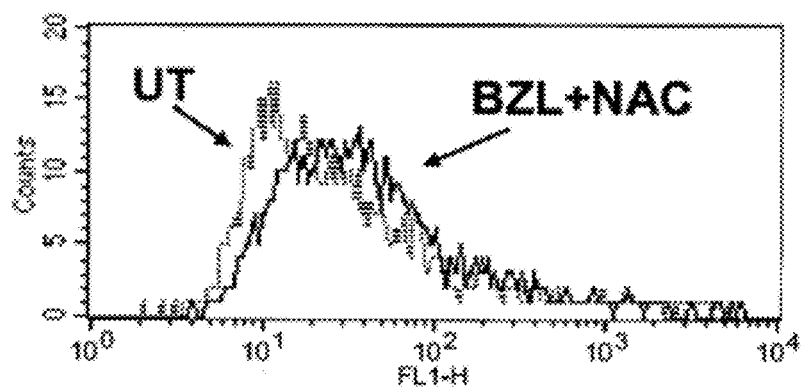
FIG. 10 shows that the conversion of non-fluorescent CM-H$_2$DCFDA into fluorescent compound is indeed due to ROS. Incubation of cells with ROS scavenger N-acetyl-cysteine (NAC) prior to addition of BZL101 prevented most of the increase in ROS generation.

BZL101 was evaluated for antiproliferative activity on five breast cancer cell lines (SK-BR-3, MCF7, MDA-MB-231, BT-474, and MCNeuA). These cell lines represent important prognostic phenotypes of breast cancer expressing a range of estrogen and HER2 receptors. BZL101, tested at a 1:10 dilution (15 g/ml), demonstrated >50% growth inhibition on four of the five cell lines (Campbell, 2002). BZL101 showed >50% growth inhibition on a panel of lung, prostate and pancreatic cancer cell lines. BZL101 at the same dose did not cause >25% of growth inhibition on normal human mammary cells (HuMEC), demonstrating selectivity to cancer cells (Table 3). Moreso, BZL101 had a mild mitogenic effect on normal human lymphocytes. In cell cycle analysis, BZL101 caused an S phase burst and G1 arrest. (See FIG. 8). BZL10 also attenuated mitochondrial membrane potential causing caspase-independent high molecular grade (HMG) apoptosis. (See FIG. 7).

The results of this in vitro experiment are summarized in Table 3, below.

TABLE 3

| Lung | | Pancreas | | Prostate | | Breast | | | | | |
|---|---|---|---|---|---|---|---|---|---|---|---|
| A549 | LLC | Panc-1 | Panc-2 | PC-3 | LNCaP | MCF7 | BT474 | SKBR3 | MDA-MB-231 | MCNeuA | HuMEC |
| + | + | + | ++ | + | + | ++ | + | ++ | + | ++ | − |

Table 3: In vitro growth inhibitory effect of BZL101 aqueous extract of *Scutellaria Barbata* 1:10 dilution − <50% inhibition, + 51-75% inhibition, ++ >75% inhibition. BZL is active on all cancer cell lines but is not active on HuMECs.

Induction of Apoptosis

To assay for DNA fragmentation as a marker of apoptosis, a procedure for the isolation of genomic DNA that allows for the analysis of both high and low molecular weight DNA fragmentation during apoptosis was used. MCNeuA cells were plated at $5 \times 10^5$ cells/well in 6-plates and allowed to adhere overnight. Aqueous herbal extracts were added to each well at a 1:10 and a 1:50 dilution. Sterile water, diluted 1:10 in culture medium, was added to the control wells. After 24 hours, the cells were visually examined under a microscope and morphological changes noted. Attached and floating cells were harvested, washed with cold PBS and embedded in lysis buffer (50 mM NaCl, 20 mM Tris HCl, pH 8.0, 20 mM EDTA, 0.5% sodium sarkosyl, 50 μg/ml RNase A and 100 μg/ml proteinase K) for 1 hour at 37° C. The cells were then washed with PBS and distilled water and placed in the wells of a conventional 1% agarose gel and electrophoresed overnight at approximately 1 V/cm. The gels were then stained with Example 1

Purification of an Extract of *Scutellaria barbata* D. Don

A purified extract of *Scutellaria barbata* D. Don, BZL102, is prepared by the following method. The liquid drug substance manufacturer receives a lot of the herb. Samples of the lot are retained and stored. The herb lot is inspected for foreign materials and adulterants. The raw herbs are evaluated for macroscopic and microscopic characteristics and are compared to a voucher specimen. A sample is extracted in methanol and compared to a voucher specimen with thin layer chromatography. Qualitative assessment of bands resolved with a calorimetric developing reagent is performed to confirm identity. Additionally, extended characterization is performed using HPLC and HPLC/MS to confirm taxonomic marker compounds.

| Marker compounds identifiable in BZL by HPLC and HPLC/MS | | | | |
|---|---|---|---|---|
| Marker Compound | M.W. | Empirical Formula | CAS Number | Structure |
| Baicalein | 270.2 | $C_{15}H_{10}O_5$ | 491-67-8 | 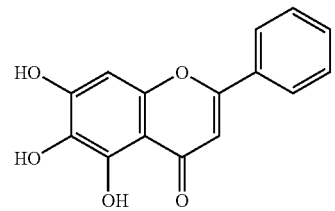 |

-continued

Marker compounds identifiable in BZL by HPLC and HPLC/MS

| Marker Compound | M.W. | Empirical Formula | CAS Number | Structure |
|---|---|---|---|---|
| Scutellarein | 286 | $C_{15}H_{10}O_6$ | 529-53-3 | 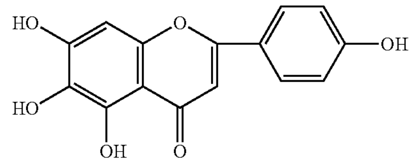 |
| scuttelarein-7-O-glucoronide (Scutellarin) | 462 | $C_{21}H_{18}O_{12}$ | 27740-01-8 | 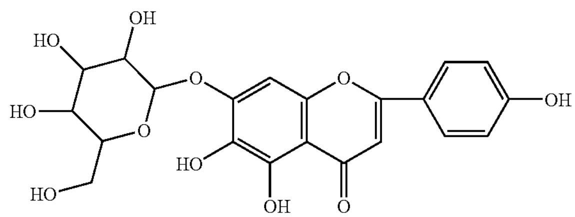 |

Finally, tests are performed to determine heavy metal, microbial, aflatoxin, and pesticide levels.

General Quality Control testing of BZL raw herb.

| Test | Tentative Specification | Method |
|---|---|---|
| Loss on Drying | <14% | KP Chemistry SOP MFT01 |
| Total Ash Content | <14% | KP Chemistry SOP MFT01 |
| Acid-Insoluble Ash | <4% | KP Chemistry SOP MFT01 |
| % solids extracted (water) | >10% | KP Chemistry SOP MFT01 |
| % solids extracted (dilute ethanol) | >10% | KP Chemistry SOP MFT01 |
| Lead (Pb) | <10 ppm | KP ICP SOP MFHM01 |
| Cadmium (Cd) | <0.3 ppm | KP ICP SOP MFHM01 |
| Chromium (Cr) | <2 ppm | KP ICP SOP MFHM01 |
| Mercury (Hg) | <0.2 ppm | KP ICP SOP MFHM01 |
| Arsenic (As) | <5 ppm | KP ICP SOP MFHM01 |
| Aflatoxin: Total Aflatoxin ( | <10 ppb | KP HPLC SOP MFA01 |
| Aflatoxin: B1 | <5 ppb | KP HPLC SOP MFA01 |
| Pesticides: Total BHCs | <0.9 ppm | KP HPLC SOP MFP01 |
| Pesticides Total DDTd | <0.1 ppm | KP HPLC SOP MFP01 |
| Pesticides: PCNB (Quintozene) | <1 ppm | KP HPLC SOP MFP01 |
| Microbial Load: aerobic bacteria | $<10^7$ CFU/g | KP Micro SOP MFM01 |
| Microbial Load: E. coli | $<10^2$ CFU/g | KP Micro SOP MFM01 |
| Microbial Load: salmonellae | Absent (0/g) | KP Micro SOP MFM01 |

Next, 300 kg of raw S. barbata is mixed with 3000 liters of deionized water. The mixture is heated to 100° C. The temperature is lowered to 70° C. and is simmered for 60 minutes. The warm extract is filtered through an 80 mesh filter.

The extract is next transferred to an evaporator where it is subject to evaporation for at 40° C. The concentrated extract is concentrated to about 60 liters. The concentrated extract is filtered over a 325 mesh filter to remove any particles. The concentrated extract is then cooled to room temperature. Finally, the cooled extract is packaged and shipped frozen to BioNovo.

Samples of the extract are tested to ensure that the extract has not been compromised during shipment or customs clearance.

Quality Control testing of BZL102 liquid drug substance.

| Test | Tentative Specification | Method |
|---|---|---|
| Loss on Drying | >30% | KP Chemistry SOP MFT01 |
| pH | 4.7-5.7 | KP Chemistry SOP MFT01 |
| Active Compound: Acteoside (verbascoside) | TBD | BioNovo LC/MS |
| Active Compound: scuttelarein-7-O-glucoronide (scutellarin) | TBD | BioNovo LC/MS |
| Active Compound: scuttelarein | TBD | BioNovo LC/MS |
| Active Compound Ratio: Acteoside: (scutellarin + scutellarein) | TBD | Computation |
| Microbial Load: aerobic bacteria | <10000 CFU/g | KP Micro SOP MFM01 |
| Microbial Load: E. coli | Absent (0/g) | KP Micro SOP MFM01 |
| Microbial Load: salmonella | Absent (0/g) | KP Micro SOP MFM01 |

Then, the extract is shipped to the powder drup substance manufacutrer. The powder drug substance manufacturer thaws the extract at 2° C. The thawed extract is pooled and diluted about 3 fold with purified water. The diluted extract is mixed to homogeneity. The diluted extracted is pumped to multiple bulk freeze drier poly-lined trays and frozen. The trays are loaded onto the drier and dried. After drying, each tray is milled. Then, the milled product is shipped to the drug product manufacturer.

Quality Control Testing of BZL102 Powdered Drug Substance

| Test | Tentative Specification | Method |
|---|---|---|
| Appearance | Fine granular dark brown powder | Visual |
| % Moisture | Average <3.5% | USP-NF <921> |
| Residue on Ignition | TBD | USP-NF<281> |
| Fingerprint (UV and TIC) | Compares to standard | LC/MS or GC/MS |
| Cell Proliferation Assay | TBD | BioNovo CyQuant |

-continued

Quality Control Testing of BZL102 Powdered Drug Substance

| Test | Tentative Specification | Method |
|---|---|---|
| Active Compound: Acteoside (verbascoside) | TBD | BioNovo LC/MS |
| Active Compound: scuttelarein-7-O-glucoronide (scuttelarin) | TBD | BioNovo LC/MS |
| Active Compound: scuttelarein | TBD | BioNovo LC/MS |
| Active Compound Ratio: Acteoside: (scutellarin + scuttelarein) | TBD | Computation |
| Strength by Dry Weight | TBD | Computation |
| Heavy Metals (As, Cd, Cr, Hg, Pb) | <10 ppm each | USP-NF <231> or ICP-MS |
| Pesticides: | Below reporting limit for all analytes | Luke OC, ON, OP, CB, Pyretroid with FDA 302 extraction |
| Pesticides: | Below reporting limit for all analytes | EDBC Screen with CDFA extraction |
| Total Aerobic Microbial Count | $<10^4$ CFU/g | USP-NF <2021> |
| Molds and Yeasts | $<10^3$ CFU/g | USP-NF <2023> |

The drug product manufacturer formulates the pharmaceutical composition with a proprietary mixture of sweeteners and flavoring agents. Finally, about 6 g to 12 g of the composition are placed in a package.

Composition of the BZL102 Drug Product

| Component | Amount/dose | Amount/batch |
|---|---|---|
| BZL101 powdered drug substance | 5 g and 10 g | 53-320 kg (equivalent to 500-3000 kg of dried BZL) |
| Excipients | 1 g and 2 g | 10.6-64 kg |

Quality Control Testing of the BZL102 Drug Product

| Test | Tentative Specification | Method |
|---|---|---|
| Appearance | Fine granular dark brown powder | Visual |
| Fingerprint (UV and TIC) | Compares to standard | LC/MS or GC/MS |
| Cell Proliferation Assay | TBD | BioNovo CyQuant |
| Active Compound: Acteoside (verbascoside) | TBD | BioNovo LC/MS |
| Active Compound: scuttelarein-7-O-glucoronide (scuttelarin) | TBD | BioNovo LC/MS |
| Active Compound: scuttelarein | TBD | BioNovo LC/MS |
| Active Compound Ratio: Acteoside: (scutellarin + scuttelarein) | TBD | Computation |
| Strength by Dry Weight | TBD | Computation |
| Mycotoxins (e.g. Aflatoxins) | <20 ppb | AOAC-I 991.31 and 999.07 |
| Total Aerobic Microbial Count | $<10^4$ CFU/g | USP-NF <2021> USP-NF <2023> |
| Molds and Yeasts | $<10^3$ CFU/g | |
| Viable Specific Microorganisms: E. coli | Absent (0/10 g) | USP-NF <2022> |
| Viable Specific Microorganisms: Staphylococcus aureus | Absent (0/10 g) | |
| Viable Specific Microorganisms salmonella species | Absent (0/10 g) | |

Example 2

In Vivo (IP) Efficacy of BZL101 in a Mouse Xenograft Model

In order to demonstrate the efficacy of BZL101 in the in vivo treatment of cancer, BZL101 was evaluated in a mouse xenograft model.

Figure 5:
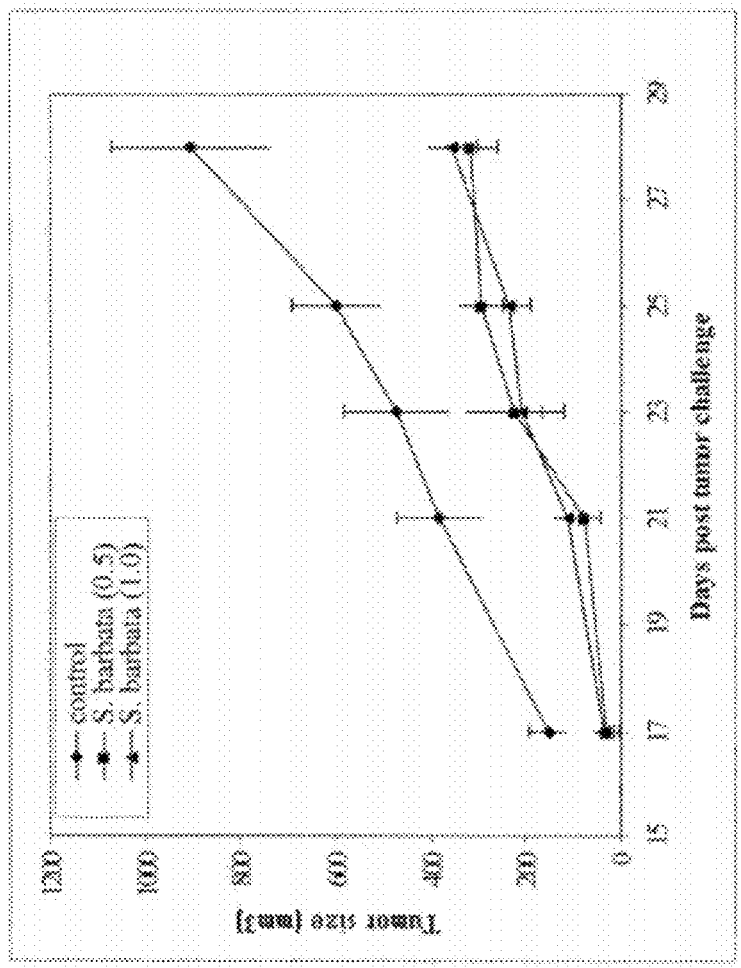
FIG. 5 shows the effect of the herb extract of the invention administered intraperitoneally (IP) on the tumors of mice in a xenograft model.
Figure 6:
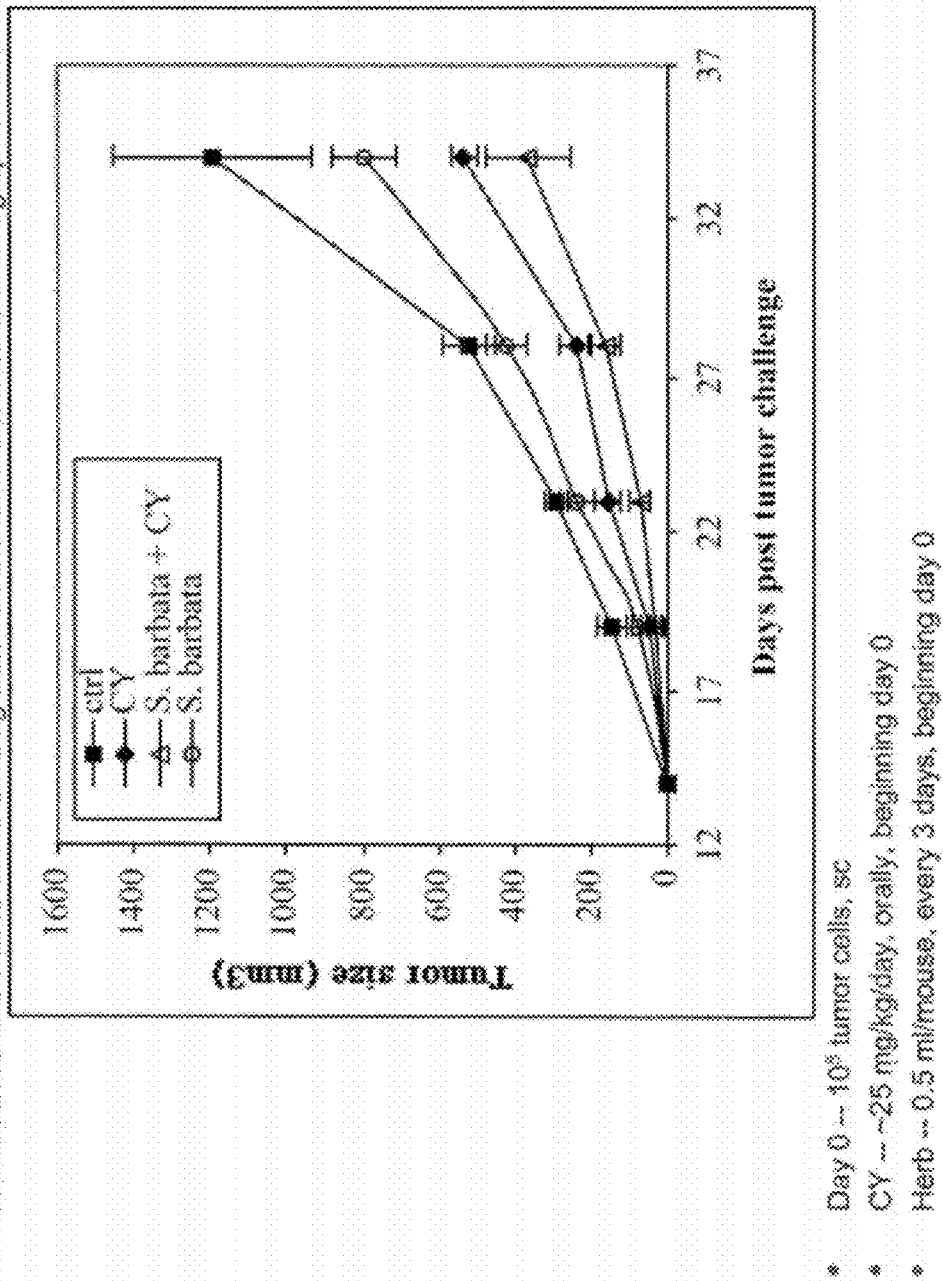
FIG. 6 shows the effect of the herb extract administered by oral gavages and in interaction with cyclophosphamide administered in low dose in the drinking water on the tumors of mice in a xenograft model.

BZL101 was active via intraperitoneal (IP) administration in preventing tumor formation in a mouse xenograft model (FIG. 5). BZL101 was prepared as described in Preparative Example 1, above. Cells ($10^5$) of MCNeuA cells were injected subcutaneously into mice on day 0. BZL101 (0.5 ml or 1.0 ml) or control was administered to each mouse IP every two days. Tumor size (mm$^3$) was estimated on the $17^{th}$, $21^{st}$, $23^{rd}$, $25^{th}$, and $28^{th}$ day post administration. The results of this study show in FIG. 5, demonstrate that BZL101 inhibited xenograft, suggesting that BZL101 can be an effective treatment for solid tumors in vivo.

Example 3

In Vivo (IP) Efficacy of BZL102 in a Mouse Xenograft Model

In order to demonstrate the efficacy of BZL102 in the in vivo treatment of cancer, BZL102 is evaluated in a mouse xenograft model.

BZL102 is obtained as described in Example 1.

BZL102 is active via intraperitoneal (IP) administration in preventing tumor formation in a mouse xenograft model. Cells ($10^5$) of MCNeuA cells are injected subcutaneously into mice on day 0. BZL102 (0.5 ml or 1.0 ml) or control is administered to each mouse IP every two days. Tumor size (mm$^3$) is estimated on the $17^{th}$, $21^{st}$, $23^{rd}$, $25^{th}$, and $28^{th}$ day post administration. The results of this study, will demonstrate that BZL102 inhibits xenograft growth, suggesting that BZL102 can be an effective treatment for solid tumors in vivo.

Example 4

Efficacy of BZL101 in Humans

In order to demonstrate the safety and clinical activity of oral BZL101, an aqueous extract from Scutellaria Barbata D. Don was studied in human patients with advanced breast cancer.

Eligible patients had histologically confirmed metastatic breast cancer and measurable disease. Patients did not receive any other chemotherapy, hormone therapy or herbal medicine during the trial. Patients received 350 ml (equivalent to 12 grams dry solubles BZL) BZL101 extract per day until disease progression, toxicity or personal preference caused them to discontinue. The primary endpoints were safety, toxicity and tumor response.

Twenty-one patients were enrolled and received BZL101. Mean age was 54 years (30-77) and mean number of prior treatments was 3.9 (0-10). There were no hematologic, nor grade III or IV non-hematologic, adverse events (AEs). Some patients reported grade I and II adverse events, such as nausea, diarrhea, headache, flatulence, vomiting, constipation, and fatigue. Sixteen patients were evaluable for response. Four of the 16 patients had stable disease (SD) for >90 days (25%) and 3/16 had SD for >180 days (19%). Five patients had minor objective tumor regression, one of which was 1 mm short of a PR based on RECIST criteria.

Patients were enrolled at the University of California, San Francisco Carol Franc Buck Breast Care Center and the Cancer Research Network in Plantation, Fla. between August 2001 and November 2004 and signed an informed consent approved by local institutional review boards. All patients were ≧18 years old with histologically confirmed diagnosis of breast cancer and clinical evidence of metastatic involvement. Patients with solitary metastases required biopsy confirmation of metastatic disease. All patients had completed prior therapies and had adequate time to recover sufficiently from the toxicities associated with prior anticancer treatments. A life expectancy of 6 months and Karnofsky performance status of 80% or better was required. Nutritional or up to five times recommended daily allowance (RDA) vitamin supplementation were permitted; but concomitant use of non-study herbal agents was prohibited. Patients were excluded from the study for the following: extensive liver involvement (>50% of liver parenchyma), lymphangitic pulmonary involvement, central nervous system involvement or spinal cord compression not stabilized by therapy for >3 months, a history of multiple or severe food or medicine allergies and organ or marrow dysfunction as defined by creatinine >2.0 mg/dl, total bilirubin >1.7 mg/dl, white blood cell count <2,500 cells/μL and platelet count <75,000 mm$^3$.

Safety monitoring was done on a continuous basis and patients were seen by a physician for examination at baseline periodically. Adverse events were graded using Common Toxicity Criteria version 2, assigned a category by organ system and coded in relation to study drug as remote, possible, probably or definitely related. Baseline tumor assessments were done within 14 days of initiation of study drug and every three months. Responses were assessed using RECIST criteria. Study drug was administered at every visit, and at this visit compliance and a review of dosages taken was performed. BZL101 extract was provided as a liquid in a sealed and labeled aluminum packet containing a full daily dose that was administered in a split dose twice a day. Daily BZL extract was administered until the determination of tumor progression or dose limiting toxicity was encountered, or until the subject decided to voluntarily discontinue, in which case, the reason for discontinuation was obtained.

RESULTS

Patient Characteristics

A total of 22 patients with advanced breast cancer consented to the study and 21 patients were treated with at least one dose of oral BZL101 and included in the safety analysis. The last patient accrued to the study was not treated with BZL101 as funding for the study from the California Breast Cancer Research Program had ended and the expiration date for the study medication was nearing. Sixteen of the patients were treated for 28 days or more and evaluable according to the Response Evaluation Criteria in Solid Tumors (RECIST). Nine subjects discontinued study medication due to patient preference, and twelve patients were removed from the study due to progression based on RECIST criteria. None of the patients were removed from the study due to either grade III or IV adverse events categorized according to the National Cancer Institute (NCI) Common Toxicity Criteria (CTC) version 2. See Table 4 for a summary of study participants and Table 5 for a summary of selected patient characteristics.

TABLE 4

Summary of Study Participants

| | |
|---|---|
| Study Participants Consented | 22 |
| Consented but not Treated with BZL101 | 1* |
| Included in Safety Analysis | 21 |
| Evaluable by RECIST Criteria | 16 |
| Off Study Due to Patient Preference | 9 |
| Off Study Due to Progression of Disease | 12 |
| Off Study Due to Grade III or IV Toxicity | 0 |

*Inventory of study medication was nearing expiration and funding for the study had ended.

TABLE 5

Summary of Baseline Characteristics: Age, Height, Weight, Race or Ethnicity

| | | |
|---|---|---|
| Age | | |
| Mean | 54.3 | years |
| Median | 55.5 | years |
| Range | 30-77 | years |
| Height | | |
| Mean | 65.2 | inches |
| Median | 65.0 | inches |
| Range | 62-68 | inches |
| Weight | | |
| Mean | 137.1 | pounds |
| Median | 139 | pounds |
| Range | 108-165 | pounds |
| Race or Ethnicity | | |
| Caucasian | 13 | (59%) |
| African American | 2 | participants (9%) |
| Hispanic | 1 | participant (5%) |
| Asian | 1 | participant (5%) |
| Native American | 1 | participant (5%) |
| Unknown | 4 | participants (18%) |

Safety Data

There were no deaths, serious adverse events or hematological adverse effects attributed to the study medication BZL101. There were no grade III or IV toxicities that were classified as possibly, probably or definitely related to BZL101.

Efficacy

Of the 21 patients who were treated with study medication, 16 patients were on the trial for 28 days or more and evaluable for response. Four of the 16 patients (25%) had stable disease for >90 days and 3/16 (19%) had stable disease for >180 days. Five patients had some degree of objective tumor regression, classified as a minimal response (<10% but <30 reduction in diameter sums). One of these responses was 1 mm short of a partial remission based on RECIST criteria. The average number of prior therapies for metastatic disease prior to treatment with the study medication, for patients who took at least one dose of BZL101, was 3.9 (See Table 6).

TABLE 6

Response to Treatment Based on RECIST Criteria

| Patient # | Age | On Study | Days on Study | Reason for Discontinuation | Prior Therapies After Diagnosis of Metastasis But Before BZL101 | NE | PD | SD | PR | CR | MR |
|---|---|---|---|---|---|---|---|---|---|---|---|
| 2001 | 48 | Aug. 28, 2001-Mar. 14, 2002 | 184 | Progression | CMF Capecitabine | | | 6 | | | 3 |
| 2002 | 30 | Oct. 02, 2001-Oct. 26, 2001 | 25 | Progression | Goserelin Anastrozole Tamoxifen Targretin trial Docetaxel AC | | <1 | | | | |

TABLE 6-continued

Response to Treatment Based on RECIST Criteria

| Patient # | Age | On Study | Days on Study | Reason for Discontinuation | Prior Therapies After Diagnosis of Metastasis But Before BZL101 | NE | PD | SD | PR | CR | MR |
|---|---|---|---|---|---|---|---|---|---|---|---|
| 2003 | 50 | Oct. 30, 2001-Apr. 17, 2002 | 151 | Pt Preference | High dose chemo Capecitabine VEGF Trial Exemestane Anastrozole Tamoxifen | | | 5 | | | 2, 3, 4 |
| 2004 | 77 | Dec. 20, 2001-Sep. 05, 2002 | 259 | Progression | None | | 9 | 6 | | | 3 |
| 2005 | 64 | Mar. 07, 2002-Apr. 11, 2002 | 36 | Pt Preference | None | | | 1 | | | |
| 2006 | 59 | Oct. 31, 2002-Jan. 09, 2003 | 71 | Pt preference | CAF Tamoxifen CMF Paclitaxel Carboplatin + Etoposide Capecitabine | NE | | | | | |
| 2007 | 60 | Dec. 09, 2002-Dec. 25, 2002 | 16 | Pt Preference | Docetaxel Trastuzamab Cisplatin Capicitabine Liposomal doxirubicin Gemcitabine | NE | | | | | |
| 2008 | 52 | Jun. 24, 2003-Aug. 21, 2003 | 59 | Pt Preference | Exemestane Tamoxifen Capecitabine | NE | | | | | |
| 2009 | 34 | Sep. 12, 2003-Oct. 28, 2003 | 41 | Progression | Doxorubicin Paciltaxel Docetaxel | | 1.5 | | | | |
| 2010 | 56 | Jun. 26, 2003-Jun. 27, 2003 | 1 | Pt Preference | Tamoxifen CAF Traztuzamab Gemcitabine Letrozole Fulvestrant | NE | | | | | |
| 2011 | 48 | Apr. 21, 2004-Jul. 23, 2004 | 93 | Progression | Docetaxil Gemcitabine | | 3 | | | | |
| 2012 | | Nov. 08, 2004-Nov. 15, 2004 | 6 | Pt Preference | Letrozole Fulvestrant Carboplatin + Docetaxel Zoledronic acid | NE | | | | | |
| 3001 | 54 | Feb. 28, 2002-Apr. 19, 2002 | 51 | Progression | Vinorelbine Traztuzamab Capecitabine | | 1.5 | | | | |
| 3002 | 48 | Feb. 28, 2002-Mar. 07, 2002 | 7 | Pt Preference | Anastrazole Letrozole | NE | | | | | |
| 3003 | 59 | Mar. 01, 2002-Nov. 15, 2002 | 260 | Progression | Liposomal doxorubicin + Paclitaxel | | 9 | | | | 1 |
| 3004 | 59 | Mar. 04, 2002-Apr. 06, 2002 | 33 | Progression | Tamoxifen Docetaxel Letrazole | | | | | | 1 |
| 3005 | 60 | Mar. 29, 2002-May 12, 2002 | 42 | Progression | Tamoxifen Letrozole Anastrozole Vinorelbine + Capecitabine NFL | | 1 | | | | |
| 3006 | 56 | Apr. 17, 2002-Jul. 01, 2002 | 63 | Progression | Tamoxifen Liposomal doxorubicin NFL Anastrozole Trastuzamab Vinorelbine Gemcitabine Capecitabine | | 2 | | | | 1 |
| 3007 | 54 | Sep. 13, 2002-Nov. 11, 2002 | 59 | Progression | TAC Tamoxifen Doxorubicin Trastuzamab Docetaxel CMF Vinorelbine Capecitabine Fulvestrant | | 2 | | | | |
| 3008 | 67 | Apr. 09, 2004-May 17, 2004 | 38 | Pt Preference | Paclitaxel Vinorelbine + Capecitabine Pfizer clinical trial Docetaxel Gemcitabine Liposomal doxorubicin | | | 1 | | | |
| 3009 | 45 | May 24, 2004-Aug. 27, 2004 | 95 | Progression | None | | 3 | | | | |
| 3010 | 59 | Not treated | 0 | | Tamoxifen Anastrozole Capecitabine Vinorelbine Liposomal doxorubicin + Gemcitabine Carboplatin + Paclitaxel Fulvestrant Toremifene Letrozole Zoledronic Acid | NE | | | | | |

Recist Criteria (Months)
NE = Not evaluable
PD = Progressive Disease,
SD = Stable Disease,
PR = Partial Remission,
CR = Complete Remission
MR = Minimal Response, >0% and <30%reduction
NFL mitoxantrone, 5-fluorouracil, leucovorin
CMF cyclophosphamide, methotrexate, fluorouracil
CAF cyclophosphamide, adriamycin, 5-fluorouracil
TAC docetaxel, adriamycin (doxorubicin), cyclophosphamide
AC adriamycin (doxorubicin), cyclophosphamide In a modified RECIST evaluation, where all measurable lesions were included as evaluable, one patient had a partial response or a reduction of 31% in the sum of the longest tumor diameter of all measurable lesions after 7 weeks of treatment and a reduction of 33% after 11 weeks of treatment (Table 7).

TABLE 7

Patient #2003 Response to Treatment Based on Modified RECIST Criteria

| DATE | Lesion 1 Site and Method Measurement | Lesion 2 Site and Method Measurement | Lesion 3 Site and Method Measurement | Lesion 4 Site and Method Measurement | Total Measurable Disease |
|---|---|---|---|---|---|
| #2003 Baseline Oct. 30, 2001 | Site: Lymph Node-Left Subclavian Method: Palpation Measurement: 3.0 × 2.5 cm | Site: Lymph Node-Anterior Cervical Method: Palpation Measurement: 2.0 × 2.0 cm | Site: Lymph Node-Left Subclavian, Post Cervical Method: Palpation Measurement: 0.8 cm | Site: Vertebrae/Pelvis Method: Pelvic CT scan Bony metastases | Total Baseline Diameters = 5.8 cm |
| Month 2 Dec. 20, 2001 | Measurement: 2.0 × 2.0 cm | Measurement: 1.5 × 1.0 cm | Measurement: 0.5 cm | Site: Bone Method: Bone Scan Bony Mets | Total Sum = 4.0 cm % Change = −31% |
| Month 3 Jan. 22, 2002 | Measurement: 2.1 × 1.5 cm | Measurement: 1.5 × 1.2 cm | Measurement: 0.3 cm | Site: Bone Method: Bone Scan Bony mets grossly stable compared with Nov. 19, 2001 | Total Sum = 3.9 cm % Change = −33% |
| Month 4 Mar. 08, 2002 | Measurement: 2.0 × 1.5 cm | Measurement: 2.0 × 2.0 cm | Measurement: 0.5 cm | | Total Sum = 4.5 cm % Change = −24% |
| Month 5 Apr. 17, 2002 | Measurement: 3.0 × 2.5 cm | Measurement: 2.0 × 1.5 cm | Measurement: 0.5 cm | | Total Sum = 5.5 cm % Change = −5% |

CONCLUSION

The herbal extract BZL101 its uses for the inhibition of solid tumor cancer cells and the treatment of such cancers in patients are described herein. Although certain embodiments and examples have been used to describe the present invention, it will be apparent to those skilled in the art that changes to the embodiments and examples may be made without departing from the scope and spirit of this invention.

Example 5

Efficacy of BZL102 in Humans

In order to demonstrate the safety and clinical activity of oral BZL102, an aqueous extract from *Scutellaria Barbata* D. Don is studied in human patients with advanced breast cancer.

Eligible patients have histologically confirmed metastatic breast cancer and measurable disease. Patients do not receive any other chemotherapy, hormone therapy or herbal medicine during the trial. Patients receive 350 ml (equivalent to 12 grams dry soluble residue from 180 g BZL) BZL102 extract per day until disease progression, toxicity, or personal preference causes them to discontinue. The primary endpoints are safety, toxicity and tumor response.

A suitable cohort of patients is enrolled and receives BZL102. Mean age and standard deviation are calculated. Mean number of prior treatments may also be determined. Patients will report grade I and II adverse events, if any, such as nausea, diarrhea, headache, flatulence, vomiting, constipation, and fatigue.

Patients are enrolled and sign an informed consent approved by local institutional review boards. All patients are ≧18 years old with histologically confirmed diagnosis of breast cancer and clinical evidence of metastatic involvement. Patients with solitary metastases require biopsy confirmation of metastatic disease. Some patients may have completed prior therapies; such patients will have had adequate time to recover sufficiently from the toxicities associated with prior anticancer treatments. A life expectancy of 6 months and Karnofsky performance status of 80% or better are required. Nutritional or up to five times recommended daily allowance (RDA) vitamin supplementation are permitted; but concomitant use of non-study herbal agents is prohibited. Patients are excluded from the study for the following: extensive liver involvement (>50% of liver parenchyma), lymphangitic pulmonary involvement, central nervous system involvement or spinal cord compression not stabilized by therapy for >3 months, a history of multiple or severe food or medicine allergies and organ or marrow dysfunction as defined by creatinine >2.0 mg/dl, total bilirubin >1.7 mg/dl, white blood cell count <2,500 cells/µL and platelet count <75,000 mm$^3$.

Safety monitoring is done on a continuous basis and patients are seen by a physician for examination at baseline periodically. Adverse events are graded using Common Toxicity Criteria version 2, assigned a category by organ system and coded in relation to study drug as remote, possible, probably or definitely related. Baseline tumor assessments are done within 14 days of initiation of study drug and every three months. Responses are assessed using RECIST criteria. Study drug is administered at every visit, and at this visit compliance and a review of dosages taken is performed. BZL102 extract is provided as a liquid in a sealed and labeled aluminum packet containing a full daily dose that is administered in a split dose twice a day. Daily BZL extract is administered until the determination of tumor progression or dose limiting toxicity is encountered, or until the subject decided to voluntarily discontinue, in which case, the reason for discontinuation is obtained.

RESULTS

Patient Characteristics

Patients with advanced breast cancer, who consent to the study and are treated with at least one dose of oral BZL102 are included in the safety analysis. Patients who are treated for 28 days or more are evaluable according to the Response Evaluation Criteria in Solid Tumors (RECIST). Subjects may discontinue study medication due to patient preference; and patients may also be removed from the study due to progression based on RECIST criteria.

It is considered that BZL102 will provide an improved side effect profile as compared to BZL101. In particular, it is considered that BZL102 will provide an improvement as compared to BZL101 in one or more gastrointestinal side effects, such as nausea, vomiting, diarrhea, bloating, gas, cramping, stomach irritation (e.g. burning), constipation, anorexia, dark stool, gastrointestinal upset, flatulence and/or gagging (especially on taking the drug—BZL102 or BZL101). In some embodiments, BZL102 may also provide reduced incidence of additional side effects—as compared to BZL101 such as headache, fatigue, hot flashes, numbness and tingling, etc.

Example 6

Dose Escalation of BZL102 in Humans

In order to assess the maximum tolerated dose and to optimize the therapeutic dose of BZL102 in humans, the experimental protocol in Example 5 is repeated, except that patients are administered 1× the dose of BZL102 set forth in Example 5 for the first week of treatment, 2× the dose of BZL102 set forth in Example 5 for the second week of treatment, 4× the dose of BZL102 set forth in Example 5 for the third week of treatment, 8× the dose of BZL102 set forth in Example 5 for the fourth week of treatment, 16× the dose of BZL102 set forth in Example 5 for the fifth week of treatment and 32× the dose of BZL102 set forth in Example 6 for the sixth week of treatment. If a patient experiences an adverse event greater than a grade I or grade II adverse event, or if a patient self-selects, the dose is reduced to the dosage used in the previous week. Patient progress is followed as set forth in Example 5. For each patient, the highest dose at which the patient does not experience higher than a grade II adverse event, or the highest dose that the patient receives in the study period, is recorded as the maximum tolerated dose. The median, mean and standard deviations for the patient cohort are determined. It is considered that, due to the expected improved side effect profile for BZL102 as opposed to BZL101, the maximum tolerated dose of BZL102 will be higher, and the therapeutic effect of BZL102 will be greater, than that of BZL101.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A process for manufacturing a pharmaceutical extract of Scutellaria barbata D. Don, comprising:
   mixing Scutellaria barbata D. Don raw herb with water,
   heating the mixture,
   separating the mixture by filtration to obtain a liquid extract,
   concentrating the liquid extract,
   filtering the concentrated liquid extract to remove insoluble solids,
   diluting the concentrated liquid extract,
   freezing the diluted extract,
   drying the frozen extract, and
   milling the dried extract.

2. The process of claim 1, wherein the amount of Scutellaria barbata D. Don mixed with deionized water is in a ratio of 1:10 (w/v).

3. The process of claim 1, wherein the mixture is heated to about 100° C.

4. The process of claim 3, wherein the temperature of the mixture is reduced to about 70° C. to about 75° C.

5. A pharmaceutical composition for the treatment of cancer, comprising an extract of Scutellaria barbata D. Don, wherein the extract of Scutellaria barbata D. Don is manufactured according to the process comprising:
   mixing Scutellaria barbata D. Don raw herb with water,
   heating the mixture,
   separating the mixture by filtration to obtain a liquid extract,
   concentrating the liquid extract,
   filtering the concentrated liquid extract to remove insoluble solids,
   diluting the concentrated liquid extract,
   freezing the diluted extract,
   drying the frozen extract, and
   milling the dried extract.

6. The pharmaceutical composition of claim 5, wherein the amount of Scutellaria barbata D. Don mixed with deionized water is in a ratio of 1:10 (w/v).

7. The pharmaceutical composition of claim 5, wherein the mixture is heated to about 100° C.

8. The pharmaceutical composition of claim 7, wherein the temperature of the mixture is reduced to about 70° C. to about 75° C.

9. The pharmaceutical composition of claim 5, further comprising at least one additional ingredient selected from the group consisting of: active pharmaceutical ingredients; enhancers; excipients; and agents used to adjust the pH, buffer the composition, prevent degradation, and improve taste, appearance, or odor.

10. The composition of claim 5, consisting of one or more pharmaceutically acceptable excipients.

11. A method of treating cancer in a patient, comprising administering to the patient an effective amount of an extract of Scutellaria barbata D. Don, wherein the extract is manufactured by the process comprising:
   mixing Scutellaria barbata D. Don raw herb with water,
   heating the mixture,
   separating the mixture by filtration to obtain a liquid extract,
   concentrating the liquid extract,
   filtering the concentrated liquid extract to remove insoluble solids,
   diluting the concentrated liquid extract,
   freezing the diluted extract,
   drying the frozen extract, and
   milling the dried extract.

12. The method of claim 11, wherein the mixture is heated to about 100° C.

13. The method of claim 12, wherein the temperature of the mixture is reduced to about 70° C. to about 75° C.

14. The method of claim 11, wherein the cancer is a breast cancer.

15. The method of claim 14, wherein the breast cancer expresses nuclear estrogen receptor at a level that does not exceed a predetermined threshold.

16. The method of claim 14, wherein the breast cancer expresses nuclear estrogen receptor at a level that exceeds a predetermined threshold.

* * * * *